United States Patent
Greeley et al.

(10) Patent No.: US 11,571,714 B2
(45) Date of Patent: Feb. 7, 2023

(54) CONTINUOUS SIEVING APPARATUSES FOR PUPAE SEPARATION

(71) Applicant: Verily Life Sciences LLC, South San Francisco, CA (US)

(72) Inventors: Daniel Greeley, San Francisco, CA (US); Peter Massaro, San Carlos, CA (US); Martin Lozano, Berkeley, CA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 84 days.

(21) Appl. No.: 17/248,837

(22) Filed: Feb. 10, 2021

(65) Prior Publication Data

US 2021/0323029 A1 Oct. 21, 2021

Related U.S. Application Data

(62) Division of application No. 16/850,533, filed on Apr. 16, 2020, now Pat. No. 10,926,295.

(51) Int. Cl.
*A01K 67/033* (2006.01)
*B07B 1/34* (2006.01)
*B07B 1/46* (2006.01)

(52) U.S. Cl.
CPC .............. *B07B 1/34* (2013.01); *A01K 67/033* (2013.01); *B07B 1/469* (2013.01); *B07B 2230/01* (2013.01)

(58) Field of Classification Search
CPC ....... B07B 1/34; B07B 1/469; B07B 2230/01; A01K 67/033

(Continued)

(56) References Cited

U.S. PATENT DOCUMENTS 6,475,061 B1 * 11/2002 Huang ................... A01K 47/04
449/12
9,180,464 B2 * 11/2015 Nimmo ..................... B07B 1/12
(Continued)

FOREIGN PATENT DOCUMENTS

CN 104011197 A 8/2014
CN 105170447 A 12/2015
(Continued)

OTHER PUBLICATIONS

U.S. Appl. No. 16/850,533, Notice of Allowance, dated Oct. 23, 2020, 10 pages.
(Continued)

*Primary Examiner* — Terrell H Matthews
(74) *Attorney, Agent, or Firm* — Kilpatrick Townsend & Stockton LLP

(57) ABSTRACT

A continuous sieving apparatus is described. The continuous sieving apparatus includes an inclined sieve surface attached to a wall. The inclined sieve surface is inclined with respect to a horizontal axis for pupae to continuously flow across down the incline. A set of openings is formed in the sieve surface so as to define a set of pathways extending through the sieve surface. The set of opening are defined by a length dimension that is greater than a width dimension. When the inclined sieve surface is submerged in a liquid, a first pupa having a first cephalothorax width that is less than the width dimension is free to move through any one of the set of openings, and a second pupa having a second cephalothorax width that is greater than the width dimension is prevented from moving through the set of openings.

20 Claims, 13 Drawing Sheets

(58) Field of Classification Search
USPC .......................................................... 209/346
See application file for complete search history.

(56) References Cited

U.S. PATENT DOCUMENTS

| | | | |
|---|---|---|---|
| 9,992,983 B1 * | 6/2018 | Sobecki | ............... A01K 67/033 |
| 2002/0121045 A1 | 9/2002 | Hall | |
| 2007/0214711 A1 | 9/2007 | Mignot | |
| 2010/0282648 A1 | 11/2010 | Bailey | |
| 2015/0008163 A1 | 1/2015 | Nimmo et al. | |
| 2017/0058621 A1 | 3/2017 | Bailey | |
| 2018/0271073 A1 | 9/2018 | Sobecki et al. | |
| 2018/0271074 A1 | 9/2018 | Sobecki et al. | |
| 2018/0312554 A1 | 11/2018 | Mayfield | |
| 2018/0369867 A1 | 12/2018 | Sobecki et al. | |
| 2019/0021289 A1 | 1/2019 | Wang et al. | |
| 2019/0037819 A1 | 2/2019 | Sobecki et al. | |
| 2019/0166811 A1 | 6/2019 | Sobecki et al. | |

FOREIGN PATENT DOCUMENTS

| | | | |
|---|---|---|---|
| CN | 105750194 A | | 7/2016 |
| CN | 207721014 | | 8/2018 |
| CN | 207721014 U | * | 8/2018 |
| CN | 108620306 A | | 10/2018 |
| CN | 108620313 A | | 10/2018 |
| CN | 208390400 U | | 1/2019 |

OTHER PUBLICATIONS

Hock, "Improved Separator for the Developmental Stages, Sexes, and Species of Mosquitoes", Available online at: http://johnwhock.com/products/laboratoryequipment/larvalpupal-separator/, Model 5412 Instructions, vol. 17, No. 6, Dec. 30, 1980, 1 page.
European Application No. EP21161347.6, Extended European Search Report, dated Sep. 9, 2021, 12 pages.
U.S. Appl. No. 17/383,168, "Non-Final Office Action", dated Oct. 5, 2022, 7 pages.
Chinese Application No. 202010373109.5, "Office Action", dated Sep. 20, 2022, 15 pages.

* cited by examiner

CONTINUOUS SIEVING APPARATUSES FOR PUPAE SEPARATION

CROSS-REFERENCE TO RELATED APPLICATIONS

This application is a division of co-pending U.S. patent application Ser. No. 16/850,533, filed Apr. 16, 2020, titled "Continuous Sieving Apparatuses For Pupae Separation," the entirety of which is hereby incorporated by reference.

BACKGROUND

Generally, a sieve can be formed of a wire or plastic mesh held in a frame. The sieve can be used for straining solids from liquid or for separating coarser objects from finer objects. As objects are placed in the sieve, they can either pass through the mesh if they are of the right size or shape, or they will be retained within the frame if they are not suitably sized or shaped. Sieves can thus be used to separate different types of objects from each other according to size or shape.

SUMMARY

Various examples are described relating to sieving containers, systems including the sieving containers, methods for using the sieving containers, and methods for forming the sieving containers.

One general aspect includes an apparatus, including a frame, an actuation system connected to the frame, and an inclined sieving container connected to the actuation system. The inclined sieving container includes a sieve surface and a perimeter wall enclosing the sieve surface to define an interior volume of the inclined sieve, the sieve surface inclined with respect to a horizontal axis from a first edge of the sieve surface to a second edge of the sieve surface, the sieve surface defining a set of openings enabling movement of pupae through the set of openings from the interior volume of the inclined sieve. Individual openings of the set of openings defined by a length dimension measured along a longitudinal axis of a respective opening and a width dimension measured along a transverse axis of the respective opening, the width dimension corresponding to a cephalothorax width of a pupa, and the length dimension greater than the width dimension. The apparatus also includes a funnel positioned adjacent to an end of the sieve surface. The apparatus also includes a basin attached to the frame and including an outer wall and a bottom that together define a basin volume with an opening opposite the bottom, the basin sized to receive the inclined sieving container and to retain a liquid. The actuation system is configured to separate a population of pupae introduced into the interior volume of the inclined sieve based on size by moving the inclined sieving container along a substantially vertical lifting axis between a first position within the basin and a second position within the basin.

Another general aspect includes a system, including a sieving container having a sieve surface inclined with respect to a horizontal axis from a first edge of the sieve surface to a second edge of the sieve surface. The sieving container also includes a perimeter wall enclosing the sieve surface to define an interior volume of the sieving container. The sieving container also includes a funnel positioned adjacent to the second edge of the sieve surface to receive liquid and pupae from an upper surface of the sieve surface, where the sieve surface defines a set of openings enabling movement of pupae through the set of openings from the interior volume. Individual openings of the set of openings defined by a length dimension measured along a longitudinal axis of a respective opening, and a width dimension measured along a transverse axis of the respective opening, the width dimension corresponding to a cephalothorax width of a pupa, and the length dimension greater than the width dimension. The system also includes an actuation system connected to the sieving container, the actuation system configured to separate a population of pupae introduced into the sieving container based on size by moving the sieving container along a substantially vertical lifting axis between a first position and a second position. The system also includes a basin including an outer wall and a bottom that together define a basin volume with an opening opposite the bottom, the basin sized to receive the sieving container and to retain a liquid.

Another general aspect includes a method, including providing an inclined sieving container within a basin, the inclined sieving container including a sieving surface, a perimeter wall enclosing the sieving surface to define an interior volume of the inclined sieving container, and an outlet. The sieve surface is inclined with respect to a horizontal axis from a first edge of the sieve surface to a second edge of the sieve surface, and where the outlet is positioned adjacent the second edge and the sieve surface defines a plurality of elongated openings enabling movement of insect pupae through the plurality of elongated openings from the interior volume. A width dimension of at least one of the elongated openings corresponding to a cephalothorax width of a representative insect pupa. The method also includes adding a liquid to the basin such that at least a portion of the sieve surface is submerged in the liquid. The method also includes introducing an aqueous solution including a population of pupae into the inclined sieving container at or near the first edge of the sieve surface. The method also includes performing a sieving action to as to separate the population of pupae into a first group of pupae and a second group of pupae. The method also includes maintaining a level of the liquid within the basin as the aqueous solution is added into the inclined sieving container. Other embodiments of this aspect include corresponding devices and systems each configured to perform the actions of the methods.

Another general aspect includes a non-transitory computer-readable storage device including computer-executable instructions that, when executed by a computer system, cause the computer system to perform operations. The operations include causing the computer system to actuate an inlet valve providing a liquid and a population of pupae into an inclined sieving container within a basin, the inclined sieving container including a sieving surface and a perimeter wall enclosing the sieving surface to define an interior volume of the inclined sieving container, and an outlet. The sieve surface inclined with respect to a horizontal axis from a first edge of the sieve surface to a second edge of the sieve surface, where the outlet is positioned adjacent the second edge and the sieve surface defines a plurality of elongated openings enabling movement of insect pupae through the plurality of elongated openings from the interior volume, a width dimension of the at least one of the plurality of elongated openings corresponding to a width of a representative pupa. The instructions also cause the computer system to actuate an outlet valve of the basin such that at least a portion of the sieve surface is submerged in the liquid. The instructions also cause the computer system to provide one or more signals to an actuation system to cause the actuation system to perform a sieving action with the inclined sieving container so as to separate the population of pupae into a first group of pupae and a second group of pupae. Other embodiments of this aspect include corresponding devices and systems each configured to perform the actions of the methods.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

DETAILED DESCRIPTION

Figure 1:
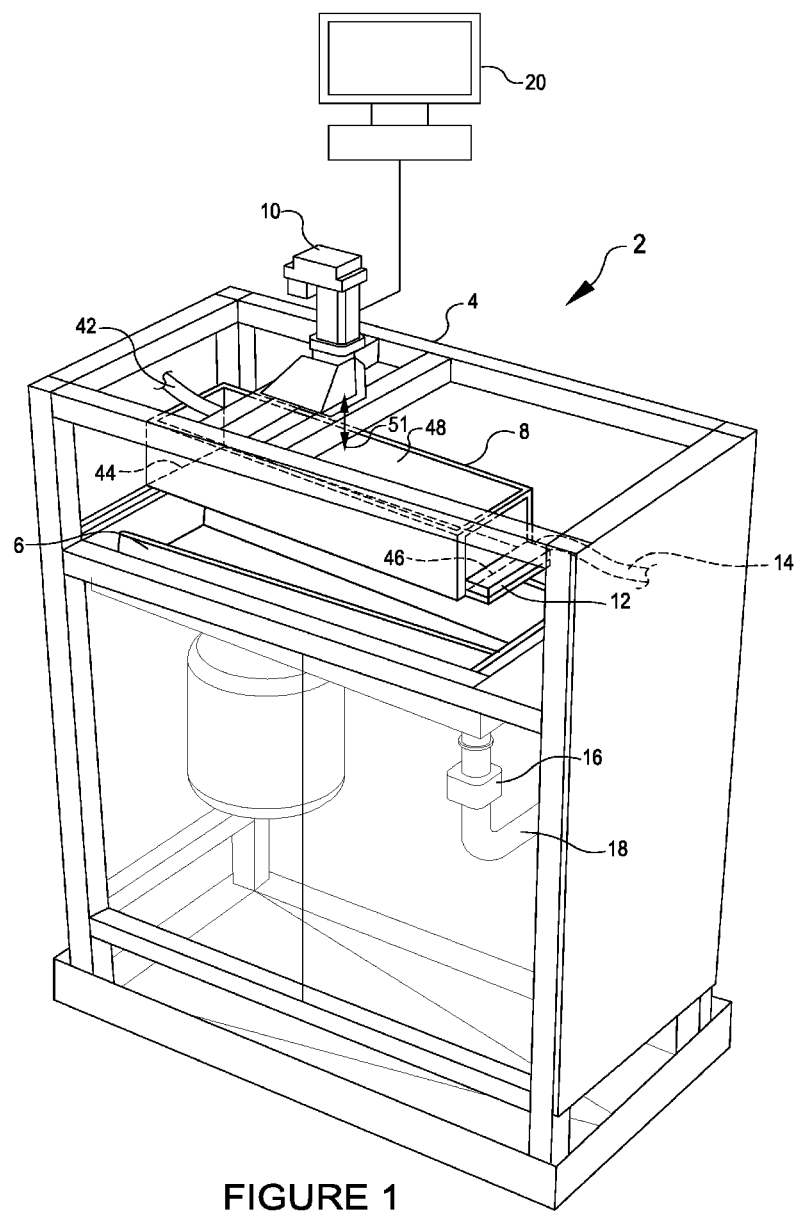
FIG. 1 illustrates a perspective view of a continuous sieving apparatus, according to at least one example.

Examples are described herein in the context of sieving containers for use in separation of insect pupae. Those of ordinary skill in the art will realize that the following description is illustrative only and is not intended to be in any way limiting. For example, the sieving containers described herein can be used to separate any insects having an aqueous pupal stage, though particular reference will be made to separation of mosquito pupae. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

In an illustrative example, a large quantity of insects are raised, such as for a sterile insect technique (SIT). The insects need to be sorted, typically into male and female insects as required for the SIT. Depending on the program, separation may be performed at one or more stages of insect development. For example, insects having an aqueous pupal stage may be separated while in the pupal stage. Typically, this sorting is performed manually or with batch processes. Use of conventional mesh screens to separate pupae may create challenges given the physiological structures of the pupae. Additionally, use of devices including parallel glass plates may create challenges given their difficulty to operate, high cost, and lack of portability. These challenges may result in prohibitively low throughput and similarly low yield. For SIT programs, manual methods and batch methods are insufficient to provide the large quantities of insects required for the program. In particular, in a mass breeding program, as part of SIT, it may be desirable to separate insects continuously and at a high quantity. The continuous sorting avoids typical batch processes that include introducing insects, sorting, clearing a sorting device, and then starting all over and instead performs the sorting process on a continuous flow of insects.

In the illustrative example, a continuous sieving apparatus for separation of pupae is described. The continuous sieving apparatus includes a rectangular sieve held within a rim. Together the sieve and the rim from a box-like structure, with the sieve forming the bottom of the box-like structure. The sieve is inclined with respect to the rim. Thus, the sieve slopes downwards in a direction from one side of the rim to another. The sieve is positioned above a basin with liquid in it and the sieve moved vertically into and out of the basin by an actuation system, which will aid in separating insect pupae as described below.

The sieve is designed to allow insect pupa of a certain size to pass through it, while retaining larger pupa (or other objects). In other words, the sieve allows the insect pupa to be sorted by size. To accomplish this, the sieve has a number of openings formed in it and the openings are sized based on the expected or desired width of the insect pupa to be sorted. For example, to separate male pupae from female pupae, the openings can be sized to be smaller than the cephalothoraxes of typical female pupae and larger than the cephalothoraxes of typical male pupae of a desired species of insect. In addition, the openings are generally designed to have an elongated shape similar to the shape of the desired male pupae. In operation, the sieve will allow the male pupae to pass through the openings, while the female pupae will slide down the inclined sieve towards a funnel, which will funnel the female pupae into an outlet into a container. Thus, the male and female pupae are separated from each other.

In operation, pupae and a liquid are poured into the sieving container, which is repeatedly moved up and down, thereby repeatedly submerging and removing the sieving container from additional liquid within the basin. As this process repeats, some pupae pass through the sieve, e.g., the male pupae, while other pupae slide down the inclined sieve towards the funnel. The incline is gradual enough that it takes multiple up-and-down actions to move a pupae down the incline. This allows enough time for the male pupae to pass through the openings so they do not reach the funnel at the end of the sieve.

The basin collects pupae and other material that passes through the sieve such as larvae, food, and other detritus, and includes one outlet to allow the pupae or other material to be removed from the basin. The basin also has a second outlet that can be used to maintain a liquid level in the basin as liquid is added into the sieve. The first outlet and the second outlet may each also be used to introduce liquid into the basin, for example to fill the basin and displace pupae to a different portion of the basin.

During operation, the continuous sieving apparatus repeatedly dunks the sieve into and out of the water in the basin to draw the pupae down onto the sieve. Because of the inclined angle of the sieve with respect to the surface of the water, the dunking causes the pupae to advance from the first edge of the sieve to the second edge of the sieve. Using this action, most, if not all, of the male pupae can pass through any one of the elongated openings, while most, if not all, of the female pupae are prevented from passing through because they are too large. The female pupae are then advanced into the funnel where they flow through an outlet to a holding tank or to a further processing system. The male pupae pass through the sieve into the basin.

In this example, the basin has two dividers to form three chambers in the basin. A central chamber is sized to receive the sieving container, and side chambers are positioned on either side of the central chamber. As the male pupae pass through the sieve, they land in liquid in the central chamber of the basin. Then, as the sieving container is again submerged into the basin, liquid and pupae or other material that has passed through the sieve are forced over the dividers into one of the side chambers, where they can then flow through an outlet into a holding container.

As the sieve is submerged in the basin, the male pupae and liquid within the central compartment are temporarily displaced and flows over the dividers of the basin to then flow out through the outlets. In some examples, the sieve may remain stationary while the basin is moved or the basin may remain stationary while the sieve is moved to submerge the sieve in the basin. The elongated shape of the openings closely corresponds to how the pupae naturally orient in still water. As water is drained through the elongated openings, those pupae already in this natural orientation remain so and those that are not are oriented by the flowing water. Sizing the elongated openings to correspond to the size and natural orientation of the pupae forces the pupae to be on a single axis of orientation to pass through the sieve. This sizing also results in high separation rates. Additionally, high separation rates are possible because, unlike mesh sieves, the sieve surface is designed to include smooth transitions between the elongated openings. This results in fewer pupae becoming entangled, e.g., by their paddles or other physiological structures, with the openings. The continuous sieving apparatus also provides high throughput for separation of pupae because it functions on a continuous cycle with an inflow of aqueous solution with pupae and an outflow of sorted pupae without having to remove the sieving container from the basin for cleaning material.

This illustrative example is given to introduce the reader to the general subject matter discussed herein and the disclosure is not limited to this example. The following sections describe various additional non-limiting examples of sieving containers.

Referring now to FIG. 1, FIG. 1 illustrates a perspective view of a continuous sieving apparatus 2, according to at least one example. The continuous sieving apparatus 2 is contained within a frame 4 and enables continuous processing and sieving of pupae to separate the pupae into subgroups, for example separating male and female pupae. The continuous sieving apparatus 2 provides high levels of throughput for sorting pupae without requiring working in batches or resetting systems or machinery and instead can operate continually. The continuous sieving apparatus 2 includes a frame 4, a basin 6, a sieving container 8, and an actuation system 10. The continuous sieving apparatus 2 receives a flow of pupae through an inlet 42 at a first edge 44 of the sieving container 8 and delivers a portion of the insect pupae out of an outlet 14 at or near a second edge 46 of the sieving container 8.

Figure 18:
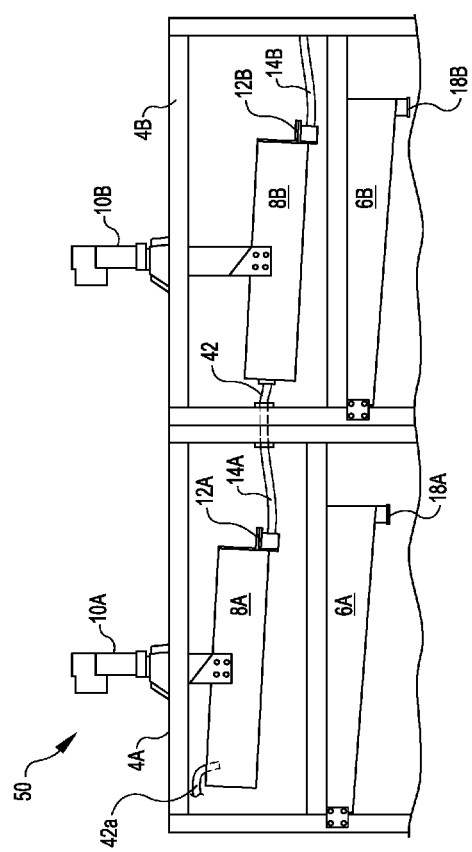
FIG. 18 illustrates an example of a continuous sieving system including two continuous sieving apparatuses, according to at least one example.

In some examples, such as depicted in FIG. 18, multiple continuous sieving apparatuses 2 may be connected in series to continuously sort the pupae. For example, a first continuous sieving apparatus 2 may separate larvae, food, and other foreign matter from the pupae while a second continuous sieving apparatus 2 may sort the pupae into male and female pupae, for example for use in an SIT program.

The frame 4 is part of a cabinet that contains elements of the continuous sieving apparatus 2. The frame 4 may include a mobile cabinet with wheels or fixtures to enable movement of the continuous sieving apparatus 2 between locations. The sieving container 8 is coupled to the frame 4 by the actuation system 10. The actuation system 10 may include a pneumatic actuator, linear actuator, ball screw, threaded rod, piston and crankshaft, or any other suitable device to generate linear motion. The actuation system 10 is connected to the frame 4 and the sieving container 8 to enable movement of the sieving container 8 relative to the frame 4. The actuation system 10 moves the sieving container 8 along a substantially vertical lifting axis 51 as shown in FIG. 1. In some examples, the actuation system 10 may move the sieving container 8 between two or more positions. For example, the actuation system 10 may actuate the sieving container 8 between a first elevation and a second elevation during a priming process, to initially establish a siphon between the outlet 14 and a destination and to initially fill the system with liquid, and may actuate the sieving container between a third elevation and a fourth elevation during a steady-state operation. The difference between the first elevation and the second elevation may be greater than a difference between the third elevation and the fourth elevation this difference may be a result of the need to initially start a flow of liquid through the system and prime the system. The actuation system 10 is controlled by a computing device 20 that may be integrated within the frame 4 or may be located remotely and control the actuation system 10 over a network such as a wireless, wired, the Internet, cellular, local, or other network type.

The sieving container 8 is described in further detail with respect to FIG. 6 below and includes a perimeter wall 48 that surrounds and retains an inclined sieve surface that together define an interior volume. Pupae in a liquid are introduced into the interior volume from above via the inlet 42 at the first edge 44 of the sieve surface. During operation, the material can slide down the inclined sieve and exit the interior volume at outlet 14 at or near the second edge 46.

The sieve surface of the sieving container 8 has a number of openings formed in it and is inclined with respect to a horizontal axis 52 of the frame 4 and inclines from the first edge 44 of the sieving container 8 to a second edge 46 of the sieving container 8 adjacent the outlet 14. At the second edge 46 of the sieving container 8, a funnel 12 extends the width of the sieving container 8 and receives pupae or material that travels across the sieve surface without passing through openings formed in the sieve surface. The funnel 12 diverts the pupae from the sieve surface to the outlet 14 where the pupae may travel to a holding tank or other system for further processing. To further help sort the pupae, in some examples, the sieving container 8 and/or the frame 4 may also include a light fixture coupled at or near the funnel 12. The light fixture may produce light to agitate, startle, or scare pupae away from the funnel 12. For example, male pupae that approach the funnel 12 without passing through the sieve surface may be frightened by the light and attempt to move away from the light and therefore also the funnel 12, thereby increasing the likelihood of passing through the openings of the sieve surface.

The basin 6 is described in further detail with respect to FIG. 4 below. But generally, the basin 6 retains a liquid such that the sieving container 8 is partially submerged as the actuation system 10 moves the sieving container 8 vertically. At one position the sieving container 8 may not be submerged at all and at a second position the sieving container 8 may be submerged, at least partially, in liquid within the basin 6 such that at least a portion of the sieve surface is submerged. The basin 6 may include an outlet 18 with a controllable valve 16, e.g., via solenoid or electric motor. The valve 16 may be actuated by a signal from the computing device 20. The computing device 20 may control the valve 16 based on a signal from a level indicator (not shown) identifying a depth of liquid within the basin 6. The basin 6 may include additional outlets and internal dividers as described below with respect to FIG. 4 to enable movement of pupae or foreign elements out of the basin 6 after they pass through the sieve surface of the sieving container 8. The outlet 18 may deliver liquid and/or other materials to a holding tank, recirculation system, or other processing system of a sterile insect technique.

Figure 2:
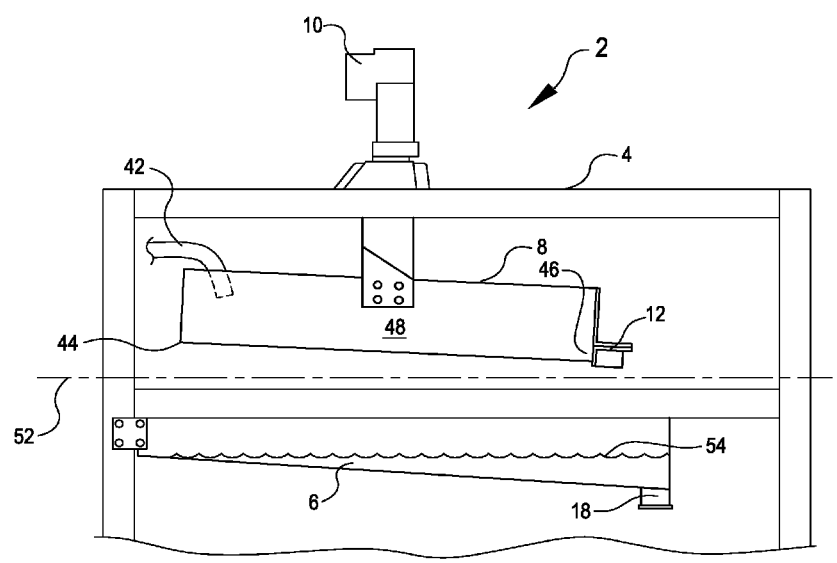
FIG. 2 illustrates a front view of a top portion of the continuous sieving apparatus of FIG. 1, according to at least one example.

FIG. 2 illustrates a front view of a top portion of the continuous sieving apparatus 2 of FIG. 1, according to at least one example. The front view shows the sieving container 8 inclined with respect to a horizontal axis 52 such that the first edge 44 of the sieving container 8, the left end in FIG. 2, is higher than the second edge 46 of the sieving container 8 adjacent the funnel 12, at the right end in FIG. 2. The sieving container 8 is inclined with respect to the horizontal axis 52 at an angle, such as less than twenty degrees. In some examples, the sieving container 8 is inclined with respect to the horizontal axis 52 at an angle of between zero and ten degrees. In some examples, the sieving container may be inclined with respect to the horizontal axis 52 at an angle of greater than ten degrees. In some examples, the angle of the sieving container 8 and the length of the sieving container 8 may be selected such that pupae that are introduced into the sieving container 8 at the left edge of the sieving container 8 (as shown in the figure) via the inlet 42 will traverse the length of the sieving container 8 after submerging the sieving container 8 between six and eight times, each time the sieving container 8 is submerged carrying pupae further along the sieving container 8. In some examples, the sieving container 8 may be adjustable with respect to the horizontal axis 52 such that the angle between the sieve surface of the sieving container 8 and the horizontal axis 52 is adjustable. In some examples, the angle may be adjustable within a range of zero to forty-five degrees such that the incline of the sieve surface can be adjusted to accommodate varying flow rates of liquid and pupae introduced into the sieving container 8.

Figure 3:
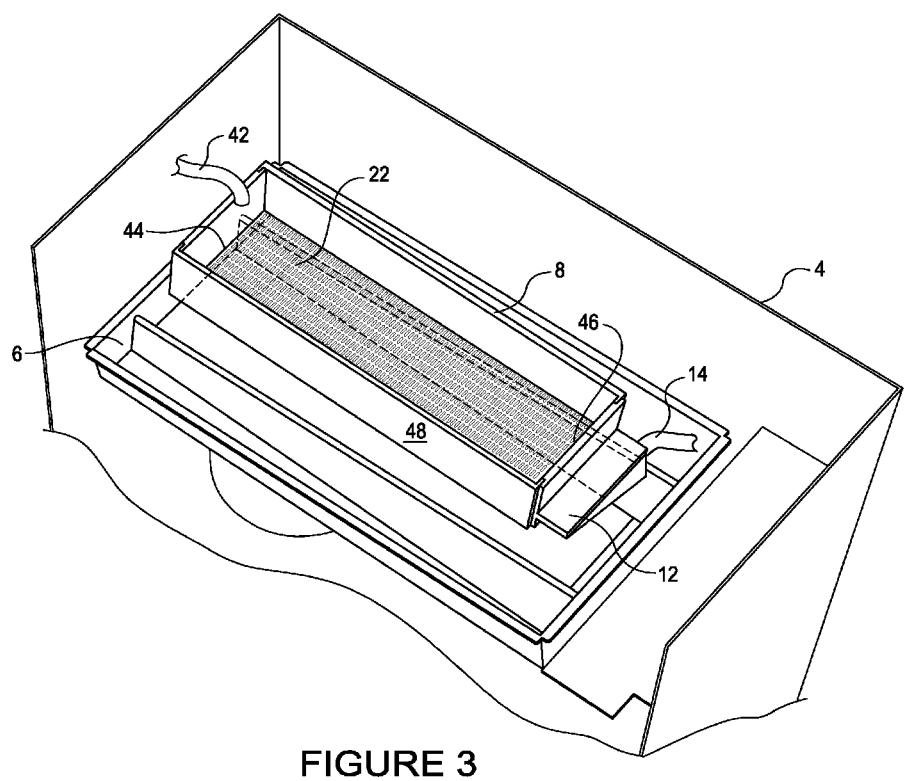
FIG. 3 illustrates a top perspective view of the continuous sieving apparatus of FIG. 1 with an upper portion removed, according to at least one example.

FIG. 3 illustrates a top perspective view of the continuous sieving apparatus 2 of FIG. 1 with an upper portion removed, according to at least one example. The top perspective view of FIG. 3 illustrates the sieving container 8 and the basin 6 with the frame 4 and the actuation system 10 cut away to provide an unobstructed view of the sieving container 8 and the basin 6. The sieving container 8 includes a sieve surface 22, described in further detail with respect to FIGS. 7 and 8 below. The basin 6 includes dividers, described with respect to FIG. 4, that define a central compartment within the basin 6 having a width greater than the width of the sieving container 8.

Figure 4:
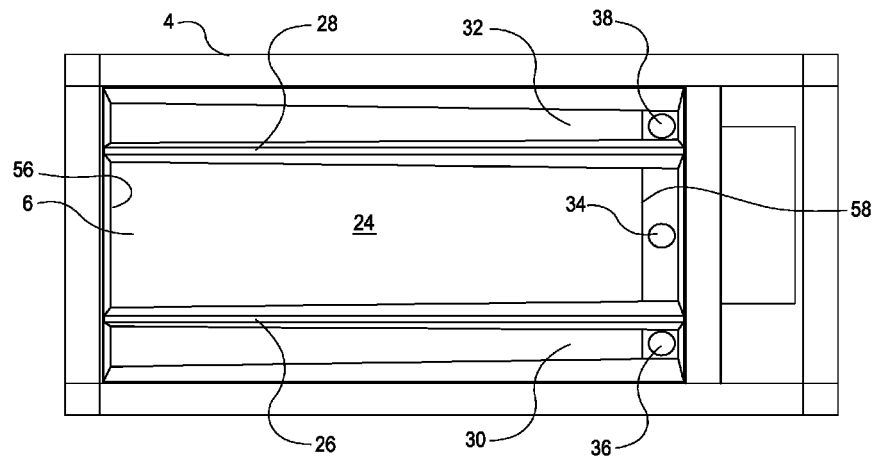
FIG. 4 illustrates a top view of the continuous sieving apparatus of FIG. 1 showing a basin of the device, according to at least one example.

FIG. 4 illustrates a top view of the continuous sieving apparatus 2 of FIG. 1 showing the basin 6, according to at least one example. The sieving container 8 and actuation system 10 are not visible in FIG. 4 to provide an unobstructed view of the basin 6. The basin 6 includes a first divider 26 and a second divider 28. The dividers 26, 28 form three compartments in the basin 6, a central compartment 24 and two edge compartments 30 and 32. The first divider 26 and the second divider 28 each extend from the bottom of the basin 6 towards the top of the basin 6. The first divider 26 and the second divider 28 extend only a portion of the height of the basin 6 such that the walls of the basin 6 extend beyond the height of the first divider 26 and the second divider 28. The lower height of the first divider 26 and the second divider 28 enables liquid within the central compartment 24 to be displaced and spill over into the edge compartments 30 and 32 when the sieving container 8 is lowered into the basin 6 and without spilling over the walls of the basin 6.

Each of the three compartments 32, 30, and 24 extends the length of the basin 6. The compartments are formed by the walls and bottom of the basin 6 as well as the first divider 26 and the second divider 28. In this example, the basin 6 has an inclined bottom, with respect to a horizontal axis 52 (shown in FIG. 2), such that liquid within the basin flows to and end of the basin 6 where outlets 34, 36, and 38 are positioned. The incline of the inclined bottom with respect to the horizontal axis 52 such that a first edge 56 of the bottom, the left end in FIG. 4, is higher than a second edge

58 of the bottom, at the right end in FIG. 4. The bottom of the basin 6 is inclined with respect to the horizontal axis 52 at an angle of less than or equal to twenty degrees. In some examples, the bottom is inclined with respect to the horizontal axis 52 at an angle equal to or greater than twenty degrees. In some examples, the angle of the bottom with respect to the horizontal may be the same as the angle of the sieving container 8 with respect to the horizontal axis 52 or may be a different angle. The central compartment 24 has a width that is greater than the width of the sieving container 8 to receive the sieving container 8 during operation of the continuous sieving apparatus 2. The width of the central compartment 24 may be near or close to the width of the sieving container 8 such that when the sieving container 8 is submerged in the liquid in the central compartment 24, the liquid level rises and spills over the first divider 26 and the second divider 28. In some examples, the central compartment 24 may be less than an inch wider than the sieving container 8 while in other examples the central compartment 24 may be greater than an inch wider than the sieving container 8.

Each of the three compartments includes an outlet 34, 36, and 38. The outlets 34, 36, and 38 provide a conduit for liquid and pupae to exit the basin 6. In operation, the outlets 36 and 38 in the edge compartments 30 and 32, may receive pupae that pass through the sieve surface of the sieving container 8 and over the first divider 26 or the second divider. In an example, male mosquito pupae may pass through the openings of the sieve surface 22 and remain within liquid contained in the central compartment 24. As liquid is displaced by movement of the sieving container 8 and spills over the first divider 26 and the second divider 28, the male pupae are carried by the liquid into the edge compartments 30 and 32. The male pupae then flow to the outlets 36 and 38 and on for processing, holding, or disposal.

The outlet 34 for the central compartment 24 may be connected with the valve 16 and the outlet 18 of FIG. 1. Outlet 34 may therefore be controllable, such as by actuating a controllable valve, to restrict or enable flow of liquid out of the central compartment 24. Outlet 34 may also be controllable to allow an inlet of water to fill the central compartment 24. In some examples, outlet 34 may be configured with a switching valve that can switch between two different connections, one for filling the central compartment 24 and another for draining the central compartment 24. The outlet 34 may be used as an inlet to control a liquid level in the central compartment 24 and displace pupae that pass through the openings of the sieve surface to the edge compartments 30 and 32. In some examples, the outlet 34 may recirculate liquid that has exited through outlets 36 and 38, for example by draining into a recirculation tank through a filter and then filling the central compartment 24 by being pumped through outlet 34. The outlet 34 may also be selectively opened to release liquid to maintain a liquid level within the central compartment 24. The liquid level may be measured with a sensor (not shown) such as a floatation sensor, a laser depth gauge, an optical sensor, an ultrasonic sensor, or other such sensor for detecting a level of liquid in the central compartment 24 or the edge compartments 30, 32. During operation, liquid released through outlet 34 may be recirculated for carrying pupae into the sieving container 8 as pupae will be carried out of the basin 6 through outlets 36 and 38 in addition to outlet 14 coupled to funnel 12. Each of the outlets 36 and 38 may also be controllable in the same manner as outlet 34, as described above.

Figure 5:
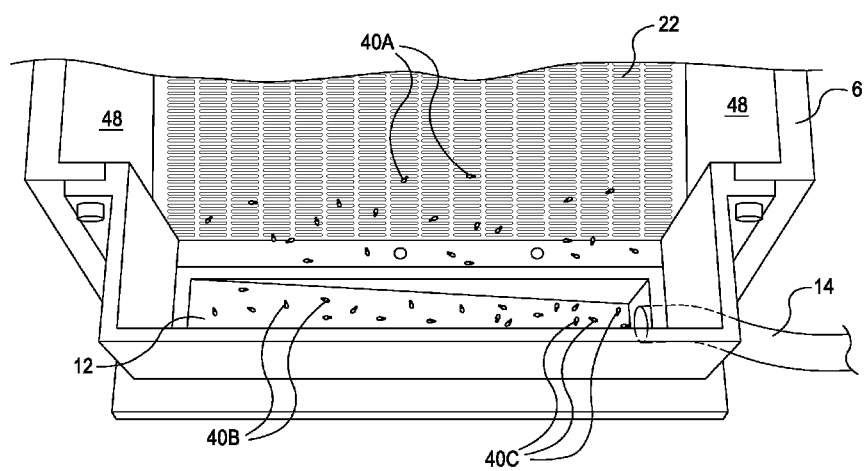
FIG. 5 illustrates a detail view of an end of a sieving surface and funnel for the continuous sieving apparatus of FIG. 1, according to at least one example.

FIG. 5 illustrates a detail view of an end of the sieve surface 22 and funnel 12 for the continuous sieving apparatus 2 of FIG. 1, according to at least one example. The funnel 12 is connected to the sieve surface such that pupae 40A travel along the inclined surface of the sieving container 8 and end up in the funnel 12. The funnel 12 receives liquid and pupae and includes a sloped or inclined surface to carry pupae 40B-40C to the outlet 14 to be transported away from the continuous sieving apparatus 2. Pupae 40B enter into the funnel 12 after traversing the sieve surface 22 and begin to travel down the slope of the funnel 12 either due to gravity or due to a siphon created traveling between the funnel 12 along the outlet 14 to a separate location such as a holding tank. The pupae 40C reach the bottom of the funnel 12 and enter the outlet 14 where they are carried by a flow of liquid through the outlet 14 to a second location. Though the funnel 12 in FIG. 5 is shown with the perimeter wall 48 extending around the edge of the funnel 12, in some examples, the perimeter wall 48 may not extend around the funnel 12, but may form an opening through which pupae and liquid may flow after traversing the length of the sieve surface 22 before entering the funnel 12. In some examples, the funnel 12 may be included within the perimeter wall 48 or at the edge of the perimeter wall 48.

Figure 6:
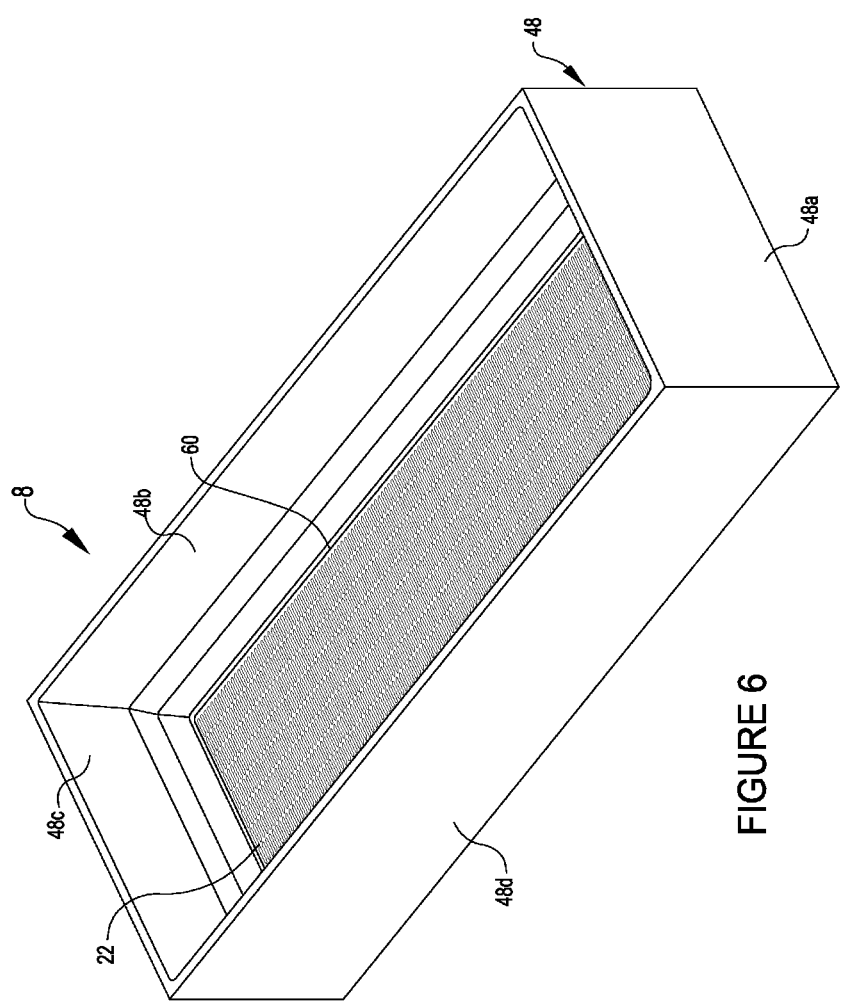
FIG. 6 illustrates a perspective view of a sieving container with a sieving surface in the bottom thereof, according to at least one example.

FIG. 6 illustrates a perspective view of a sieving container 8 with a sieve surface 22 in the bottom thereof, according to at least one example. The sieving container 8 is an example of the sieving container 8 of FIGS. 1 through 5. The sieving container 8 includes a sieve surface 22 held within a perimeter wall 48. The sieve surface 22 may be angled with respect to the perimeter wall 48. The top of the perimeter wall 48 may be parallel to the sieve surface 22. In some examples the top of the perimeter wall 48 may be at an angle with respect to the top of the perimeter wall 48. In this example, the inclination of the sieve surface 22 is formed when the sieving container 8 is connected to the actuator, such as the actuation system 10. For example, the sieving container 8 may have an upper surface at the top of the perimeter wall 48 parallel to the sieve surface 22, the sieve surface 22 may be parallel with a horizontal axis 52 (shown in FIG. 2) until connected to the actuating system, at which time the sieve surface 22 is inclined with respect to the horizontal axis 52. The perimeter wall 48 includes a plurality of walls 48a-48d that together define a volume having a rectangular cross section. The perimeter wall 48 may also form a passage for the inlet 42 which may provide a conduit for liquid and pupae to be introduced into the sieving container 8, for example from a storage tank. In some examples, the perimeter wall 48 has a non-rectangular perimeter (e.g., round, triangular, and any other suitable non-rectangular shape). The height of the perimeter walls 48 can range between 2-5". In some examples, the height of the perimeter walls 48 is greater than 5". Irrespective of the cross section and the wall height, the perimeter wall 48 can function to funnel or otherwise direct a liquid (e.g., water) through the sieve surface 22. The sieve surface 22 also includes a series of openings 62 which are described in detail with reference to later figures.

Figure 7:
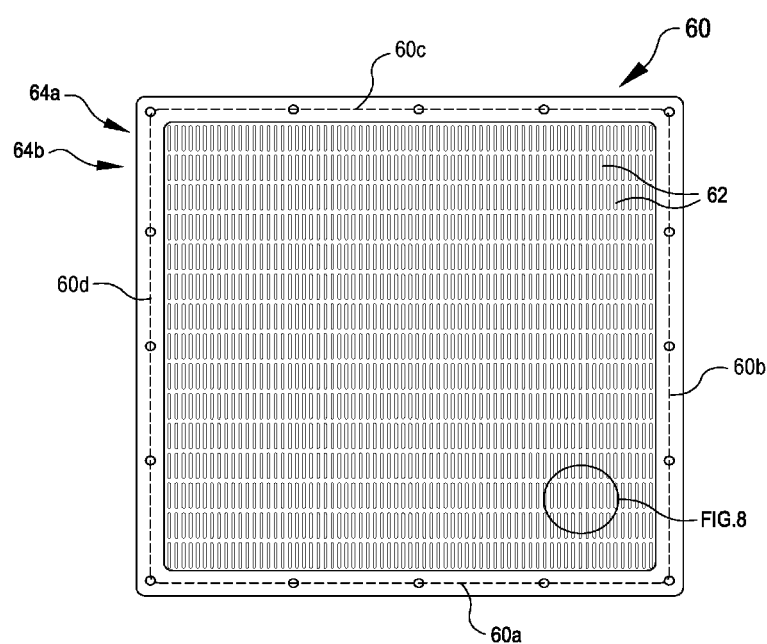
FIG. 7 illustrates a top view of a sieve surface, according to at least one example.

FIG. 7 illustrates a top view of a portion of the sieve surface 22, according to at least one example. The sieve surface 22 may be combined with additional sieve surfaces 22 placed end to end, or having a rectangular shape to form the sieve surface 22. In some examples, the sieve surface 22 may be formed from a single sheet with openings cut, machined, or stamped in the single sheet. In some examples, the sieve surface 22 may be formed of multiple sheets placed end to end, each sheet having openings therein. The sieve surface 22 can be held within a sieve frame 60. The sieve frame 60 includes a plurality of members 60a-60d that together define a rectangular cross section. In some examples, however, the sieve frame 60 may have a non-rectangular cross section. To enable coupling the sieve frame 60 to the perimeter wall 48, the cross section of the perimeter wall 48 and the cross section of the sieve frame 60 can correspond. The sieve frame 60 also provides rigidity to the sieve surface 22. In some examples, sieve frames 60 having different sieve surfaces 22 (e.g., different sized openings) can be detachably mounted to the same perimeter wall 48, depending on the implementation. For example, a kit can include multiple sieve surfaces 22 having different sized openings 62 that can be independently detachably mounted to the perimeter wall 48. In some examples, more than one sieve surfaces 22 can be held within the sieve frame 60 at any one time. For example, multiple sieve surfaces 22 having different sized openings 62 can be mounted in the perimeter wall 48 so as to separate a population of pupae into more than two groups. In some examples, multiple continuous sieving apparatuses can be used in series, each including a sieving surface having different sizes and dimensions of openings. In some examples, a sieve surface 22 can have different sizes and dimensions of openings over the length or width of the sieve surface 22. For example, the openings may increase in width over the length of the sieve surface 22 to allow different material of different sizes to pass through the sieve surface 22 into the basin at different stages. The basin may include additional compartments divided along the length of the basin to collect the material of different sizes that falls through the sieve surface 22 as a flow of material travels along the sieve surface 22.

As illustrated in FIG. 7, the openings 62 can be organized into a series of rows 64a-64N including a plurality of openings 62. A few of the rows are labeled (e.g., 64a and 64b). The openings 62 can be repeated within the rows 64 to form a row pattern. The rows 64 can be repeated within the sieve surface 22 to form a sieve surface pattern. The number and dimensions of the rows 64a-64N can be a product of the dimensions of the openings 62, spacing between the openings 62, and the material used to form the sieve surface 22. In some examples, a single row including a plurality of openings 62 is provided. In this example, the single row can extend between members 60b and 60d. The openings 62 of this single row 64 can extend longitudinally between members 60a and 60c.

In some examples, the sieve surface 22 may be formed by a plurality of elongated rods laid out between the members 60b and 60d. The ends of these rods can extend between the members 60a and 60c and be held in place by these members 60a and 60c. In this example, the openings 62 can be formed between individual ones of the plurality of elongated rods.

Figure 8:
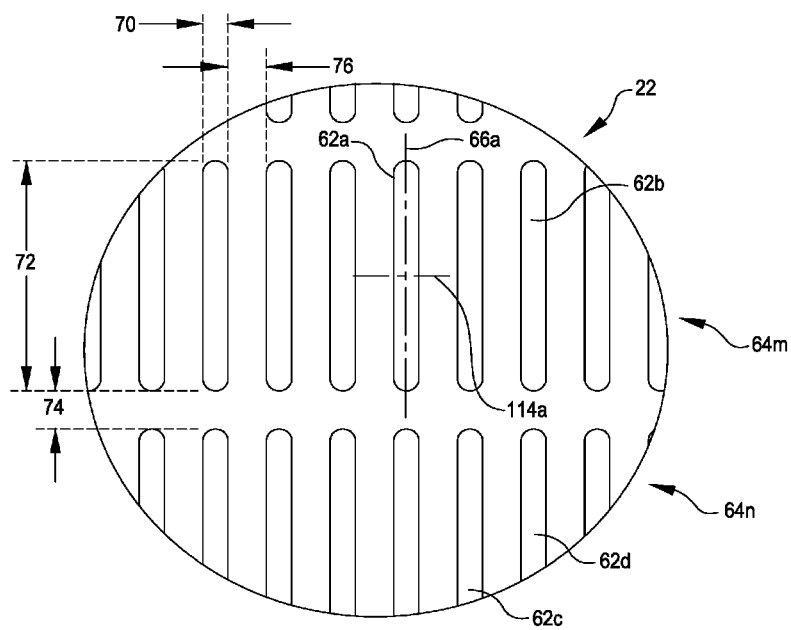
FIG. 8 illustrates a detail view of the sieving surface of FIG. 7, according to at least one example.

FIG. 8 illustrates a detailed view of the sieve surface 22, according to at least one example. The sieve surface 22 define a number of openings 62, a few of which are labeled. Each opening 62 can have a generally elongated cross section. For example, as illustrated with respect to opening 62a, the cross section can be defined by a length dimension 72 measured along a longitudinal axis 66a of the opening 62a and a width dimension 70 measured along a transverse axis 68a of the opening 62a. The length dimension 72 can be greater than the width dimension 70. As described in detail herein, a generally elongated cross section can enable selection of a smaller width dimension 70 corresponding to the smallest dimension of cephalothorax as compared to square mesh sieves, which are generally sized to the largest dimension of the cephalothorax.

A value of the width dimension 70 can be dependent on the goals of a separation program and characteristics of pupae to be separated. For example, populations of *Aedes aegypti* or *Aedes albopictus* mosquitos can be separated. As described herein, the sieving container 8 can be used to separate any species of insect that has an aquatic pupal phase. In some examples, the value of the width dimension 70 may range from 800 microns to 1500 microns, which may be appropriate for separating mosquitos. Values larger than 1500 microns and smaller than 800 microns may be appropriate for other insect species. In a particular example, the value of the width dimension 70 can be about 1200 microns. A value of the length dimension 72 can also be dependent on the goals of the separation program and characteristics of the pupae to be separated. For example, the value of the length dimension 72 may range from 2500 microns to many millimeters (e.g., 12 millimeters). For example, in the example illustrated in FIG. 3, the value of the length dimension 72 is about 10 times greater than the value of the width dimension 70. In some examples, the value of the length dimension 72 can be arbitrarily selected so long as it is greater than a largest cross-sectional dimension (e.g., tip to tail) of a typical pupa which is expected to pass through the opening 62a. Because the width dimension 70 is sized to correspond to a different smaller dimension of the typical pupa, the length dimension 72 will be larger than the width dimension 70.

The rows 64 can be spaced in accordance with a row dimension 74. For example, row 64m including the openings 62a, 62b can be spaced apart from row 64n including the openings 62c, 62d by the row dimension 74. A value of the row dimension 74 may range from 1000 microns to 3000 microns. In some examples, the value of the row dimension 74 is much greater than 3000 microns. The openings 62 can be spaced in accordance with a space dimension 76. For example, the opening 62a can be spaced apart from the opening 62b by the space dimension 76. A value of the space dimension 76 may range from about 500 microns to 3000 microns. In some examples, the value of the space dimension 76 is much greater than 3000 microns. Depending on the value of the row dimension 74, the value of the space dimension 76, the value of the length dimension 72, and the value of the width dimension 70, an example sieve surface 22 may have between 5-30 openings 62 per square inch. In some examples, the value of the row dimension 74, the value of the space dimension 76, the value of the length dimension 72, and the value of the width dimension 70 are selected to provide sufficient rigidity to the sieving container 8 and a suitable fraction of open area to solid structure (e.g., openings 62 compared to rigid portion of the sieve surface 22), while still preventing entanglement with the pupae.

In some examples, the values of the row dimension 74 and the space dimension 76 are selected to minimize or reduce a ratio of solid area to open area across the sieve surface 22. Thus, by placing the openings 62 close together (e.g., a small value of the space dimension 76) and placing the rows 64 close together (e.g., small value of the row dimension 74), a greater quantity of openings 62 and rows 64 can be formed in the sieve surface 22. This can provide for increased throughput and increased yield in a separation program.

In some examples, the values of the row dimension 74 and the space dimension 76 depends on the material selected for the sieve surface 22 and the forming method. The sieve surface 22 can be formed from any suitable material such as metal, plastic, glass, ceramic, acrylic, and other materials having similar properties. The forming technique used to form the sieve surface 22 will depend on the material selected. Example forming techniques include, but are not limited to, laser cutting, water jet cutting, photochemical etching, punching, die cutting, milling, additive manufacturing (e.g., three-dimensional printing), molding, casting, stamping, and other similar techniques.

Figure 9:
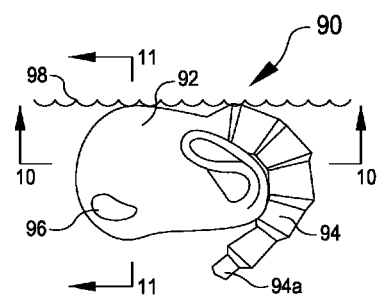
FIG. 9 illustrates a side view of an example mosquito pupa that can be separated using a continuous sieving apparatus, according to at least one example.
Figure 10:
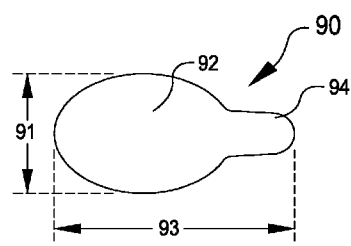
FIG. 10 illustrates a profile view of an example mosquito pupa that can be separated using a continuous sieving apparatus, according to at least one example.
Figure 11:
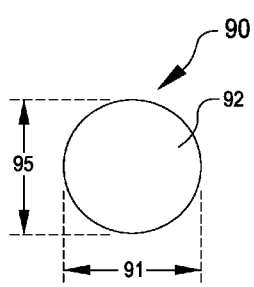
FIG. 11 illustrates a profile view of an example mosquito pupa that can be separated using a continuous sieving apparatus, according to at least one example.

FIGS. 9, 10, and 11 respectively illustrate a side view, a first profile view, and a second profile view of an example mosquito pupa 90 that can be separated using the continuous sieving apparatus 2, according to various examples. The mosquito pupa 90 includes a cephalothorax 92 and an abdomen 94. When in the pupal stage, the mosquito pupa 90 uses its abdomen 94, including a distal portion 94a, as a flipper to move through water 98. The cephalothorax 92 also includes eyes 96, one of which is illustrated and labeled. In the profile view illustrated in FIG. 10, the mosquito pupa 90 can be defined by a cephalothorax width 91 and an overall length 93. In the profile view illustrated in FIG. 11, the mosquito pupa 90 can also be defined by the cephalothorax height 95. Based on the physiological structures of the pupae (e.g., the mosquito pupa 90), the cephalothorax width 91 will be less than the overall length 93. In some examples, the cephalothorax height 95 is greater than the cephalothorax width 91. Thus, the cephalothorax width 91 can represent the narrowest dimension of the largest part (e.g., the cephalothorax 92) of the mosquito pupa 90.

As introduced herein, the value of the length dimension 72 of the openings 62 can be selected based on the overall length 93. For a given pupal population, a minimum value for the length dimension 72 should be greater than the overall length 93 of the expected largest pupa in the population. In some examples, a value of the length dimension 72 is much greater the overall length 93 of the largest pupa (e.g., an order of magnitude of 10 to 100 times greater).

As introduced herein, the value of the width dimension 70 of the openings 62 can be selected based on the cephalothorax width 91. For example, assume for a moment that a goal of a separation program is to separate male mosquito pupae from female mosquito pupae. In this example, if an example male population has an average cephalothorax width 91 of 1100 microns and an example female population has an average cephalothorax width 91 of 190 microns. Given this difference of 300 microns between the average cephalothorax widths and given a difference of about 50 microns between a female mosquito with the smallest cephalothorax width 91 (e.g., 1250 microns) in the female population and a male mosquito pupa with the largest cephalothorax width 91 (e.g., 1200 microns) in the male population, a value for the width dimension 70 can be selected to give a high probability of separation. In this example, a value of 1200-1225 microns for the width dimension 70 can be suitable.

In the view illustrated in FIG. 9, the mosquito pupa 90 is oriented in a natural orientation, one in which the mosquito pupa 90 will naturally orient when located within the water 98. In this orientation, the mosquito pupa 90 is able to obtain oxygen at the surface of the water 98 via respiratory trumpets (not shown) that extend from an upper portion of the cephalothorax 92 (e.g., near the upper surface of the water 98). This orientation may be referred to as a "tail-down orientation" because the distal portion 94a of the abdomen 94 (e.g., a tail) points down.

Figure 12:
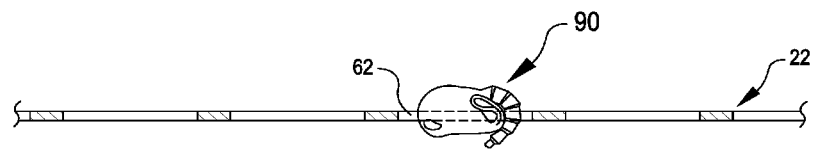
FIG. 12 illustrates a side view of a mosquito pupa passing through an opening of a sieve surface, according to at least one example.

FIG. 12 illustrates a side view of the mosquito pupa 90 passing through the opening 62 in the sieve surface 22, according to at least one example. In the example illustrated in FIG. 12, the mosquito pupa 90 is oriented in the tail-down orientation as the mosquito pupa 90 passes through the opening 62.

Figure 13:
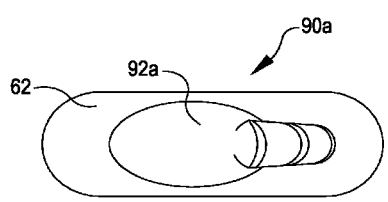
FIG. 13 illustrates a mosquito pupa aligned in a first orientation with respect an opening of a sieve surface, according to at least one example.
Figure 14:
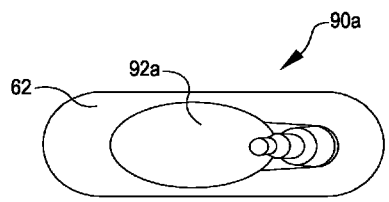
FIG. 14 illustrates a mosquito pupa aligned in a second orientation with respect an opening of a sieve surface, according to at least one example.

FIGS. 13 and 14 respectively illustrate a first mosquito pupa 90a in a first orientation and a second orientation with respect an opening 62, according to various examples. In particular, the first mosquito pupa 90a is shown passing through the opening 62. This is because the cephalothorax width 91 of a first cephalothorax 92a is less than a value of the width dimension 70. The first orientation of the first mosquito pupa 90a illustrated in FIG. 13 is an example of the tail-down orientation illustrated in FIGS. 9 and 12. The second orientation of the first mosquito pupa 90a illustrated in FIG. 14 is an example of a tail-up orientation. This may constitute a rotation of about 180 degrees.

Figures 15, 16:
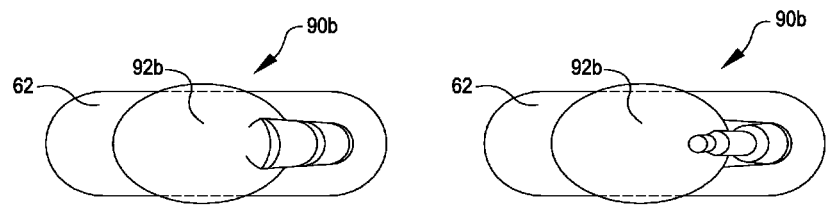
FIG. 15 illustrates a mosquito pupa aligned in a first orientation with respect an opening of a sieve surface, according to at least one example.
FIG. 16 illustrates a mosquito pupa aligned in a second orientation with respect an opening of a sieve surface, according to at least one example.

FIGS. 15 and 16 respectively illustrate a second mosquito pupa 90b in a first orientation and a second orientation with respect an opening 62, according to various examples. In particular, the second mosquito pupa 90b is shown as being prevented from passing the opening 62. This is because the cephalothorax width 91 of a second cephalothorax 92b is greater than a value of the width dimension 70. The first orientation of the second mosquito pupa 90b illustrated in FIG. 15 is an example of the tail-down orientation illustrated in FIGS. 9 and 12. The second orientation of the second mosquito pupa 90b illustrated in FIG. 16 is an example of the tail-up orientation. This may constitute a rotation of about 180 degrees.

In some examples, the openings 62 of the sieve surface 22 are sized such that the first mosquito pupae 90a can pass through the openings 62 and the second mosquito pupae 90b are prevented from passing through the openings 62. For example, the first mosquito pupae 90a may be male pupae and the second mosquito pupae 90b may be female pupae. In some examples, the first mosquito pupae 90a is a first set of male (or female) pupae and the second mosquito pupae 90b is a second set of male (or female) pupae.

In some examples, the openings 62 of the sieve surface 22 are sized such that the first mosquito pupae 90a can pass through the openings 62 in any one of the tail-down or tail-up orientations and the second mosquito pupae 90b are prevented from passing through in any orientation. In some examples, the openings 62 are sized such that the first mosquito pupae 90a may pass through in other orientations as well (e.g., head down or abdomen down).

Figure 17:
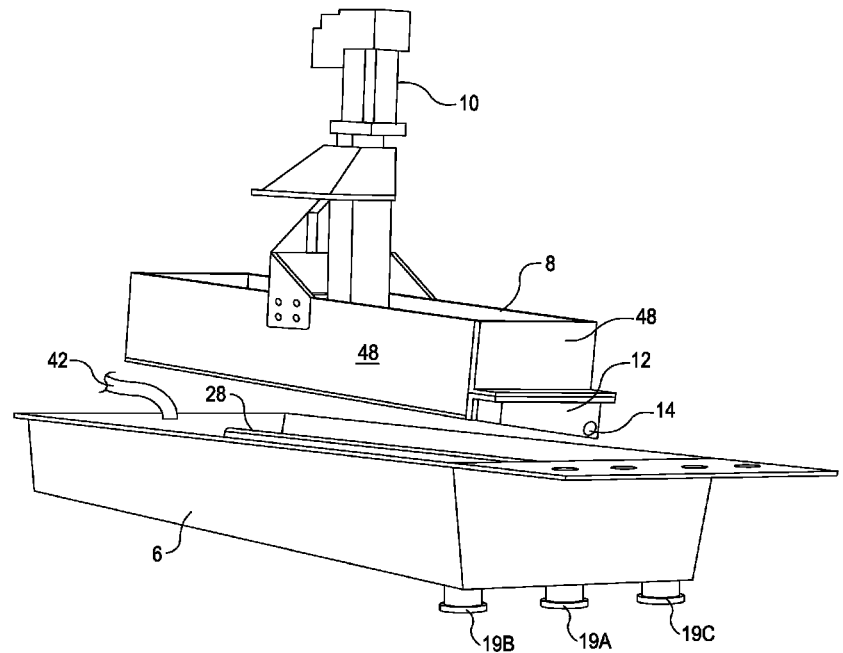
FIG. 17 illustrates a perspective view of a continuous sieving apparatus with a frame hidden to show elements of the apparatus, according to at least one example.

FIG. 17 illustrates a perspective view of a continuous sieving apparatus 2 with a frame 4 hidden to show elements of the device, according to at least one example. The continuous sieving apparatus 2 includes a sieving container 8 with perimeter walls 48, a basin 6, outlets 19A-19C, funnel 12, and outlet 14, as well as actuation system 10 to move the sieving container 8 between different vertical positions with respect to the basin 6. In operation, the sieving container 8 is placed inside the basin 6 and liquid has been added to the basin 6. Additionally, liquid may be continually introduced into the sieving container 8, for example at the inlet 42. In any event, the liquid is introduced and pupae are introduced into the sieving container 8 with the liquid at the inlet 42 The outlets 19A-19C are examples of the outlet 18 from the basin 6 described above with respect to FIG. 2. The outlets 19A-19C may each have valves that may be actuated to control a flow of liquid out of the compartments of the basin 6.

In some examples, outlet 19A also enables liquid to flow into the basin, for example to fill the central compartment of the basin. The outlet 19A may therefore be connected to both a drain and a liquid line and include a valve capable of switching between a draining operation and a filling operation, such as a switching valve that connects outlet 19A to a water line and a disposal line. Liquid may be pumped in to the basin through outlet 19A to displace floating pupae over the dividers 26 and 28 of the basin 6 by increasing the liquid level, to move pupae into the side compartments 30 and 32 for exiting through outlets 19B and 19C.

In some examples, the population of pupae introduced into the sieving container 8 have been previously raised within a lab, captured in the wild, or otherwise acquired. The population of pupae can include pupae having varied characteristics. For example, the population of pupae can include pupae of various sexes, of various sizes, of various species, and the like.

The sieving container 8 can be raised vertically by the actuation system 10 so as to remove the sieve surface 22 from the liquid in the basin 6. In some examples, this action constitutes a sieving action which causes the population of pupae to be drawn down towards the sieve surface 22 and along the sieve surface 22 towards the funnel 12 in a continuous manner as the liquid drains through openings (e.g., the openings 62) of the sieve surface 22 and into the basin 6. Repeating this sieving action one or more times may cause the population of pupae to separate into a first pupa group and a second group of pupae. The first group of pupae may be those pupae of the population that are small enough to pass through the openings 62 of the sieve surface 22. For example, the first group of pupae may include male mosquito pupae. The second group of pupae may be those pupae of the population that are too large to pass through the openings 62 of the sieve surface 22. For example, the second group of pupae may include female mosquito pupae.

The sieving action includes changing an elevation of the sieve surface 22 with respect to the liquid within the basin 6. In some examples, the sieving action includes changing a level of the liquid with respect to the sieve surface 22 rather than moving the sieve surface 22. For example, the liquid can be drained from the basin 6 and recirculated into the basin 6. In some examples, the liquid is drained from the basin 6 and new liquid is added to the basin 6, wither with or separate from the introduction of pupae with liquid.

During a priming or startup operation, the sieve surface 22 of the sieving container is initially submerged to a bottom position by the actuation system 10 and subsequently raised to a high position wherein the sieving container 8 is fully removed or nearly fully removed from the liquid within the basin 6. At the priming stage, the time interval and rate of speed for moving the sieving container 8 may be relatively slow, compared to a steady state operation. For example, at steady state the sieving container 8 may be moved between an upper and a lower position in less than half of a second, while during the priming stage the sieving container 8 may be moved between the bottom position to the high position in greater than half of a second. The initial priming phase causes liquid to flow toward and into the funnel 12 and through the outlet 14 to initiate a siphon action between the funnel and the exit of the outlet 14. The siphon action may move the pupae from the funnel 12 and thereby not require pumping or forcing that may damage the pupae.

After an initial priming stage, the sieving container 8 may be moved between the bottom position and a steady-state upper position. The steady state upper position may be lower than the high position of the priming phase. Additionally, the rate or frequency of actuation of the sieving container 8 into and out of the liquid may increase as the system transitions from the priming phase to a steady state phase. The actuation rate or rate of submerging the sieving container 8 may be configured to allow pupae to contact or interface with the openings 62 of the sieve surface 22 in a range of four to ten times, or more particularly between six and eight times before reaching the funnel 12. This may be accomplished by altering the angle of the sieving container 8 with respect to the horizontal axis 52 as described above as well as by altering the rate at which the sieving container 8 is submerged within the liquid. Ensuring that pupae interface with or contact the sieve surface 22 multiple times ensures that the pupae are oriented in the proper direction to pass through the openings at least once.

The use of the continuous sieving apparatus 2 can continue until a source of pupae to be sorted through the sieve is depleted, enabling quick and continuous separation of pupae with high yield rates as compared to conventional or batch techniques. Large number of mosquito pupae, on the order of tens of thousands, can be separated based on size in less than a minute for as long as the continuous sieving apparatus 2 is in operation.

In some examples, the continuous sieving apparatus 2, or multiple continuous sieving apparatus 2 connected in series, can be used for separating the first group of pupae and the second group of pupae into one or more subgroups. For example, sieving containers 8 having sieve surfaces 22 with differently sized openings 62 can be used in sequence to further refine the separation of the pupae. For example, the second group of pupae which did not pass through the first sieve surface 22 can be sieved again using a sieve surface of a second continuous sieving apparatus 2, after passing through the outlet 14 and into an inlet of the second continuous sieving apparatus, with larger openings than the first sieve surface 22. The sieving process can be repeated to sort precisely by size differential. This process can also be performed in reverse, where the largest sieve surface 22 is used first, and sequentially moving to smaller and smaller sieve surfaces 22, and with the processed pupae sorted through the outlets 19A-19C. In addition, varying sizes of openings 62 in sieve surfaces 22 may be used to sort foreign material from pupae and subsequently to sort pupae of varying sizes, as illustrated in FIG. 18.

FIG. 18 illustrates an example of a continuous sieving system 50 including two continuous sieving apparatuses 2, according to at least one example. The continuous sieving apparatuses 2 each include the elements described above and differ with respect to the size of the openings of the sieve surfaces 22 within the sieving containers 8. The use of multiple continuous sieving apparatuses 2 enables the continuous sieving system 50 to sort out foreign material such as food and larvae as well as sort pupae based on size in a single continuous process without the need to change out machinery, parts, or work in batches. The outlet 14 of the first continuous sieving apparatus 2A feeds an inlet 42 of the second continuous sieving apparatus 2B.

In some examples, based on the size of the openings, the actuation rate of the sieving container 8 may be adjusted. For example, a sieve surface 22 with larger openings may allow liquid to pass through more quickly than a sieve surface 22 with smaller openings. As such, the actuation or submerging rate of the sieve surface 22 with larger openings may be greater than the actuation rate of the sieve surface 22 with smaller openings.

While the example shown in FIG. 18 illustrates two continuous sieving apparatuses in series, any number of continuous sieving apparatuses may be connected in series.

Figure 19:
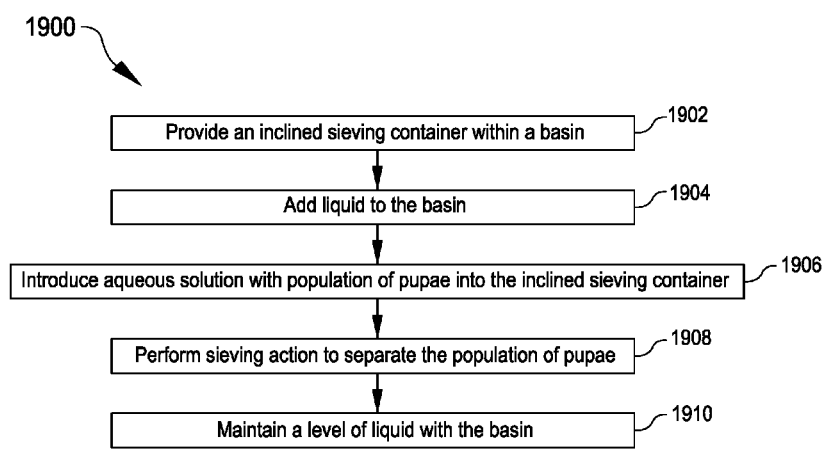
FIG. 19 illustrates an example process for separating a population of pupae based on size, according to at least one example.

FIG. 19 illustrates an example process 1900 for separating a population of pupae based on size, according to at least one example. The process 1900 can be performed using the continuous sieving apparatus 2 or any other comparable system. The process 1900 can be performed in a continuous manner, as insect pupae are continuously introduced into the continuous sieving apparatus 2.

The process 1900 begins at 1902 by providing an inclined sieving container within a basin. The inclined sieving container may be the sieving container 8 described above. The sieving container can include a sieve surface inclined with respect to a horizontal axis from a first edge to a second edge and a sieve rim or perimeter wall as well as a funnel adjacent the second edge. In the sieve surface can be formed a plurality of elongated openings. The sieve surface can be attached to the perimeter wall. In some examples, the plurality of elongated openings form a plurality of pathways extending through the sieve surface. The elongated openings of the plurality of elongated openings can be defined by a length dimension and a width dimension. The length dimension can be measured along a longitudinal axis of each elongated opening. The width dimension can be measured along a transverse axis of each elongated opening. In some examples, the length dimension is larger than the width dimension. In some examples, a value of the width dimension corresponds to a cross-sectional cephalothorax width of a typical pupa of the first group of pupae, such as a cephalothorax width of a male or female mosquito pupa.

At 1904, the process 1900 includes adding a liquid to the basin such that at least a portion of the sieve surface adjacent the second edge is submerged in the liquid. In some examples, the liquid is water.

At 1906, the process 1900 includes continuously introducing an aqueous solution with a population of pupae into the inclined sieving container. The aqueous solution is continuously introduced at or near the first edge of the inclined sieving container (e.g., within an interior volume of the box-like structure of the inclined sieving container). In some examples, the pupae are disposed within water that is poured into the interior volume of the inclined sieving container. In some examples, the population of pupae are treated with a larvicide prior to being added to the sieving container. This ensures any larvae still present in the population are dead prior to going through the sieving process. The population of pupae are continuously introduced to be sorted by the continuous sieving device, this enables high throughputs and flow rates to increase a sorting rate over typical methods.

At 1908, the process 1900 includes performing a sieving action so as to separate the population of pupae into a first group of pupae and a second group of pupae.

In some examples, the sieving action includes raising and lowering the sieving container relative to the liquid in the basin and between a first elevation at which a first portion of the sieve surface is submerged in the liquid, and a second elevation at which a second portion of the sieve surface is removed from the liquid, the second portion of the sieve surface larger than the first portion. In some examples, the sieving action is performed as quickly as one cycle per every two seconds (e.g., one second down and one second up). In some examples, the cycle time is determined based on the time it takes for the liquid to drain through the sieve surface and fill the sieve rim. Thus, the cycle time may depend on the open area of the sieve surface and the volume of the sieve rim. The sieving action may be performed by an actuation system, such as actuation system 10 connected to the inclined sieving container. The sieving action is continuously performed, though may be performed at different frequency rates and with varying magnitudes of movement between a top position and bottom position of the sieving container.

At 1910, the process 1900 includes maintaining a level of liquid within the basin. As liquid with pupae is introduced into the inclined sieving container, the liquid level within the basin increases and may be measured by a sensor. A computing device may receive the liquid level reading from the sensor and instruct a controllable valve to selectively open to maintain a liquid level within the basin to maintain consistent sieving action and performance as the inclined sieving container is moved between the first and second positions.

In some examples, the process 1900 can further include allowing the population of pupae to migrate from the second edge of the sieve surface into a funnel and through an outlet.

Figure 20:
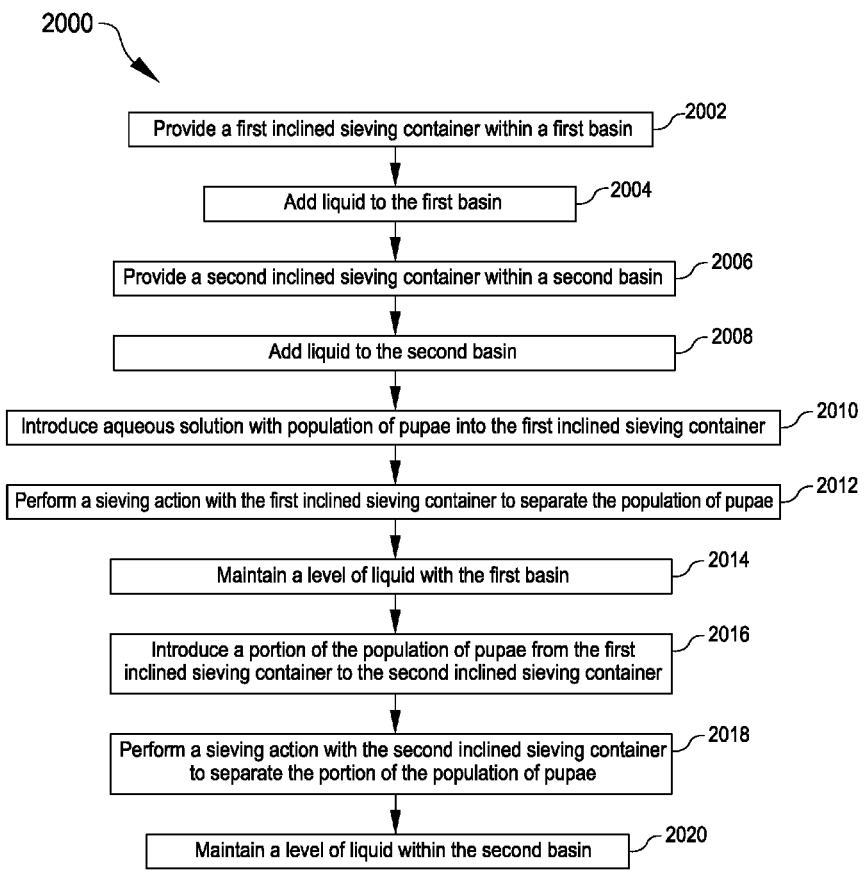
FIG. 20 illustrates an example process for separating a population of pupae using sequential continuous sieving apparatuses, according to at least one example.

FIG. 20 illustrates an example process 2000 for separating a population of pupae based on size, according to at least one example. The process 2000 can be performed using multiple continuous sieving apparatuses 2, such as in continuous sieving system 50. The process 2000 enables continuous sieving of insect pupae without requiring working in batches or stopping to clear the sieve surface.

The process 2000 begins at 2002 by providing a first inclined sieving container within a basin. The inclined sieving container may be the sieving container 8 described above. The sieving container can include a sieve surface inclined with respect to a horizontal axis from a first edge to a second edge and a sieve rim or perimeter wall as well as a funnel adjacent the second edge. In the sieve surface can be formed a plurality of elongated openings. The sieve surface can be attached to the perimeter wall. In some examples, the plurality of elongated openings form a plurality of pathways extending through the sieve surface. The elongated openings of the plurality of elongated openings can be defined by a length dimension and a width dimension. The length dimension can be measured along a longitudinal axis of each elongated opening. The width dimension can be measured along a transverse axis of each elongated opening. In some examples, the length dimension is larger than the width dimension. In some examples, a value of the width dimension corresponds to a cross-sectional cephalothorax width of a typical pupa of the first group of pupae, such as a cephalothorax width of a male or female mosquito pupa.

At 2004, the process 2000 includes adding a liquid to the basin such that at least a portion of the sieve surface adjacent the second edge is submerged in the liquid. In some examples, the liquid is water.

At 2006, the process 2000 includes providing a second inclined sieving container within a second basin. The second inclined sieving container and the second basin may be similar to the first inclined sieving container and the first basin, with an exception that the openings within the sieve surface of the second sieving container are sized differently than the openings of the first sieving container. In some examples the first openings may be larger in at least one dimension than the second openings. In some examples, the first openings may be smaller in at least one dimension than the second openings. The second inclined sieving container may be provided with an inlet coupled to an outlet of the first inclined sieving container such that material that either does or does not pass through a sieve surface of the first inclined sieving container is provided to the inlet of the second inclined sieving container. In some examples, the material that passes through the first sieve surface may be discarded and the material that does not pass through, including pupae, passed on to the second sieving container for further sorting based on size. In some examples, only material that passes through the first sieve surface may be provided to the second inclined sieving container.

At 2008, the process 2000 includes adding a liquid to the second basin such that at least a portion of the sieve surface of the second inclined sieving container adjacent the second edge is submerged in the liquid. In some examples, the liquid is water.

At 2010, the process 2000 includes continuously introducing an aqueous solution with a population of pupae into the first inclined sieving container. The aqueous solution is introduced at or near the first edge of the inclined sieving container. In some examples, the pupae are be disposed within water that is poured into the portion of the liquid. In some examples, the population of pupae are treated with a larvicide prior to being added to the sieving container. This ensures any larvae still present in the population are dead prior to going through the sieving process.

At 2012, the process 2000 includes continuously performing a sieving action with the first inclined sieving container so as to separate the population of pupae into a first group of pupae and a second group of pupae. The sieving action may be substantially the same sieving action described above with respect to FIG. 19.

At 2014, the process 2000 includes maintaining a level of liquid within the first basin. As liquid with pupae is introduced into the inclined sieving container, the liquid level within the basin increases and may be measured by a sensor. A computing device may receive the liquid level reading from the sensor and instruct a controllable valve to selectively open to maintain a liquid level within the basin to maintain consistent sieving action and performance as the inclined sieving container is moved between the first and second positions.

At 2016, the process 2000 includes continuously introducing a portion of the population of pupae from the first inclined sieving container to the second inclined sieving container. As described above, this may include first sorting foreign material or larvae from pupae at the first inclined sieving container and subsequently sorting pupae by size at the second inclined sieving container. In some examples, the pupae may be sorted by size at the first inclined sieving container and subsequently further sorted based on size into sub-groups at the second inclined sieving container.

At 2018, the process 2000 includes maintaining a level of liquid within the second basin. As liquid with pupae is introduced into the second inclined sieving container, the liquid level within the basin increases and may be measured by a sensor. A computing device may receive the liquid level reading from the sensor and instruct a controllable valve to selectively open to maintain a liquid level within the basin to maintain consistent sieving action and performance as the inclined sieving container is moved between the first and second positions.

Figure 21:
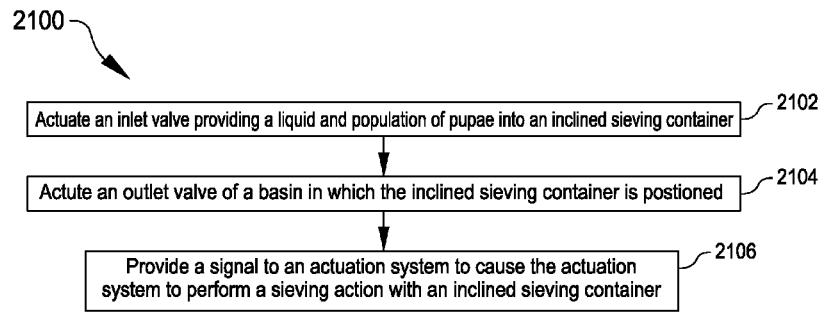
FIG. 21 illustrates an example methods for controlling a continuous sieving apparatus, according to at least some examples.

Referring now to FIG. 21, FIG. 21 illustrates a flowchart for an example method for controlling a continuous sieving apparatus, according to at least some examples. The process 2100 is performed by the computing device 20, in connection with elements of the continuous sieving apparatus 2; however it may be performed using any suitable system according to this disclosure. The continuous sieving apparatus continuously sorts insect pupae from a flow of insect pupae in a liquid that is introduced into the continuous sieving apparatus.

This process, and other processes described herein, are illustrated as logical flow diagrams, each operation of which represents a sequence of operations that can be implemented in hardware, computer instructions, or a combination thereof. In the context of computer instructions, the operations may represent computer-executable instructions stored on one or more non-transitory computer-readable storage media that, when executed by one or more processors, perform the recited operations. Generally, computer-executable instructions include routines, programs, objects, components, data structures and the like that perform particular functions or implement particular data types. The order in which the operations are described is not intended to be construed as a limitation, and any number of the described operations can be combined in any order and/or in parallel to implement the processes.

Additionally, some, any, or all of the processes described herein may be performed under the control of one or more computer systems configured with specific executable instructions and may be implemented as code (e.g., executable instructions, one or more computer programs, or one or more applications) executing collectively on one or more processors, by hardware, or combinations thereof. As noted above, the code may be stored on a non-transitory computer readable storage medium, for example, in the form of a computer program including a plurality of instructions executable by one or more processors.

At 2102, the process 2100 includes actuating, by the computing device 20, an inlet valve to provide a liquid and a population of pupae into an inclined sieving container, such as inclined sieving container 8 and includes a perimeter wall enclosing a sieving surface and forming an interior volume of the inclined sieving container. The inclined sieving container also includes an outlet, the sieve surface inclined towards the outlet, from a first edge of the sieve surface to a second edge of the sieve surface. Actuating the inlet valve enables control of the flow rate of liquid, such as water, and pupae into the inclined sieving container. The flow rate may be controlled in a range from one to two liters per minute to several hundred liters per minute.

At 2104, the process 2100 includes actuating an outlet valve of a basin that receives the inclined sieving container, the basin is an example of basin 6. The outlet valve of the basin may be actuated to maintain or control a level of liquid within the basin such that at least a portion of the sieve surface is submerged in the liquid. The outlet valve may be actuated based on a liquid level signal from a liquid level sensor positioned in or adjacent the basin.

At 2106, the process 2100 includes providing a signal to an actuation system to cause the actuation system to perform a sieving action with the inclined sieving container. The inclined sieving container may be actuated into and out of the liquid within the basin. The sieving action may separate the population of pupae into a first group of pupae and a second group of pupae based on the size of the pupae. In some examples, the actuation system may initially prime the system by actuating the inclined sieving container between a first position and a second position, the first position with the sieve surface at least partially submerged and the second position with the sieve surface submerged to a lesser degree or not at all submerged. The priming action may allow the funnel and outlet of the inclined sieving container to establish a siphon between the funnel and a final destination, thereby eliminating the need for a pump to remove liquid and pupae from the inclined sieving container.

After the initial priming phase, the actuation system may move the inclined sieving container between two positions, closer together than the first position and the second position, the sieve surface at least partially submerged over the entire cycle.

Figure 22:
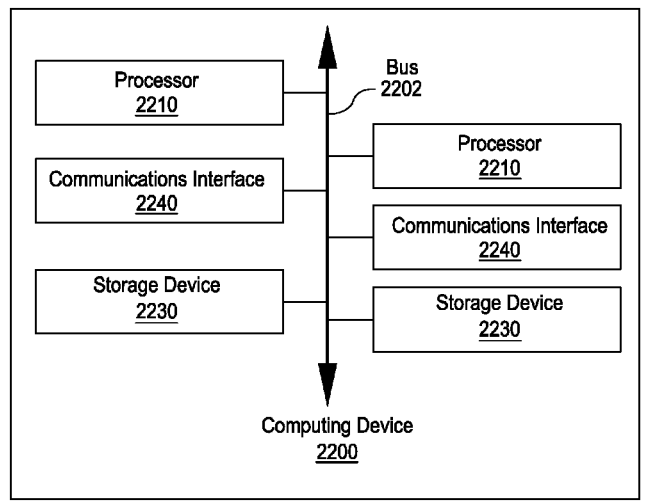
FIG. 22 illustrates a block diagram of a computing device for implementing processes and methods described herein, according to at least some examples.

Referring now to FIG. 22, FIG. 22 illustrates a block diagram of computing device 2200 for implementing processes and methods described herein, according to at least some examples. For example, computing device 2200 may be the computing device 20 of FIG. 1 or other computing devices included herein. Computing device 2200 includes a processor 2210 which is in communication with the memory 2220 and other components of the computing device 2200 using one or more communications buses 2202. The processor 2210 is configured to execute processor-executable instructions stored in the memory 2220 to perform an authorization check of the surgical tool according to different examples, such as part or all of the example processes 1900, 2000, and 2100 described above with respect to FIGS. 19, 20, and 21. The computing device 2200, in this example, also includes one or more user input devices 2270, such as a keyboard, mouse, touchscreen, microphone, etc., to accept user input. The computing device 2200 also includes a display 2260 to provide visual output to a user.

The computing device 2200 can include or be connected to one or more storage device 2230 that provides non-volatile storage for the computing device 2200. The storage device 2230 can store system or application programs and data used by the computing device 2200, such as software implementing the functionalities provided by the processes 1900, 2000, and 2100. The storage device 2230 might also store other programs and data not specifically identified herein.

The computing device 2200 also includes a communications interface 2240. In some examples, the communications interface 2240 may enable communications using one or more networks, including a local area network ("LAN"); wide area network ("WAN"), such as the Internet; metropolitan area network ("MAN"); point-to-point or peer-to-peer connection; etc. Communication with other devices may be accomplished using any suitable networking protocol. For example, one suitable networking protocol may include the Internet Protocol ("IP"), Transmission Control Protocol ("TCP"), User Datagram Protocol ("UDP"), or combinations thereof, such as TCP/IP or UDP/IP.

While some examples of methods and systems herein are described in terms of software executing on various machines, the methods and systems may also be implemented as specifically configured hardware, such as field-programmable gate array (FPGA) specifically to execute the various methods. For example, examples may be implemented in digital electronic circuitry, or in computer hardware, firmware, software, or in a combination thereof. In one example, a device may include a processor or processors. The processor includes a computer-readable medium, such as a random access memory (RAM) coupled to the processor. The processor executes computer-executable program instructions stored in memory, such as executing one or more computer programs. Such processors may include a microprocessor, a digital signal processor (DSP), an application-specific integrated circuit (ASIC), field programmable gate arrays (FPGAs), and state machines. Such processors may further include programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

Such processors may include, or may be in communication with, media, for example computer-readable storage media, that may store instructions that, when executed by the processor, can cause the processor to perform the steps described herein as carried out, or assisted, by a processor. Examples of computer-readable media may include, but are not limited to, an electronic, optical, magnetic, or other storage device capable of providing a processor, such as the processor in a web server, with computer-readable instructions. Other examples of media include, but are not limited to, a floppy disk, CD-ROM, magnetic disk, memory chip, ROM, RAM, ASIC, configured processor, all optical media, all magnetic tape or other magnetic media, or any other medium from which a computer processor can read. The processor, and the processing, described may be in one or more structures, and may be dispersed through one or more structures. The processor may include code for carrying out one or more of the methods (or parts of methods) described herein.

In the following, further examples are described to facilitate the understanding of the present disclosure.

Example 1. In this example, there is provided a device comprising a frame; an actuation system connected to the frame; an inclined sieving container connected to the actuation system, the inclined sieving container comprising: an inclined sieve comprising a sieve surface and a perimeter wall enclosing the sieve surface to define an interior volume of the inclined sieve, the sieve surface inclined with respect to a horizontal axis from a first edge of the sieve surface to a second edge of the sieve surface, the sieve surface defining a set of openings enabling movement of pupae through the set of openings from the interior volume of the inclined sieve, individual openings of the set of openings defined by: a length dimension measured along a longitudinal axis of a respective opening; and a width dimension measured along a transverse axis of the respective opening, the width dimension corresponding to a cephalothorax width of a pupa, and the length dimension greater than the width dimension; a funnel positioned adjacent to an end of the sieve surface; and a basin attached to the frame and comprising an outer wall and a bottom that together define a basin volume with an opening opposite the bottom, the basin sized to receive the inclined sieving container and to retain a liquid, wherein the actuation system is configured to separate a population of pupae introduced into the interior volume of the inclined sieve based on size by moving the inclined sieving container along a substantially vertical lifting axis between a first position within the basin and a second position within the basin.

Example 2. In this example, there is provided a device of any of the preceding or subsequent examples, wherein, when the sieve surface is submerged in the liquid: a first pupae having a first cephalothorax width that is less than the width dimension is free to move through any one of the set of openings; and a second pupae having a second cephalothorax width that is greater than the width dimension is prevented from moving through any one of the set of openings.

Example 3. In this example, there is provided a device of any of the preceding or subsequent examples, wherein the sieve surface is inclined with respect to the horizontal axis at an angle of less than fifteen degrees.

Example 4. In this example, there is provided a device of any of the preceding or subsequent examples, wherein the sieve surface comprises a constant incline from the first edge to the second edge.

Example 5. In this example, there is provided a device of any of the preceding or subsequent examples, wherein: moving the inclined sieving container along the substantial vertical lifting axis between the first position and the second position is configured to cyclically submerge the sieve surface in the liquid; the sieve surface has a first length and is inclined with respect to the horizontal axis at a first angle; and the first length and the first angle are configured to cause a pupa to traverse the sieve surface over a period of between six and eight cycles of submerging the sieve surface.

Example 6. In this example, there is provided a device of any of the preceding or subsequent examples, wherein the pupa is a mosquito pupa.

Example 7. In this example, there is provided a device of any of the preceding or subsequent examples, wherein the apparatus comprises a mobile cart with the frame attached thereto.

Example 8. In this example, there is provided a device of any of the preceding or subsequent examples, wherein moving the inclined sieving container along the substantial vertical lifting axis between the first position and the second position is configured to cyclically submerge the sieve surface in the liquid, wherein an upper portion of the perimeter wall is not submerged in the liquid while the sieve surface is cyclically submerged.

Example 9. In this example, there is provided a device of any of the preceding or subsequent examples, wherein moving the inclined sieving container along the substantial vertical lifting axis between the first position and the second position is configured to cyclically submerge the sieve surface in the liquid, wherein a portion of the sieve surface is not submerged in the liquid for at least a period of time while cyclically submerging in the liquid.

Example 10. In this example, there is provided a device of any of the preceding or subsequent examples, wherein moving the inclined sieving container along the substantially vertical lifting axis between the first position and the second position is configured to advance the population of pupae along the sieve surface towards the funnel.

Example 11. In this example, there is provided a device of any of the preceding or subsequent examples, wherein repeated movement between the first position and the second position causes the population of pupae present in the interior volume to be separated into a first group of pupae and a second group of pupae.

Example 12. In this example, there is provided a device of any of the preceding or subsequent examples, wherein: the first group of pupae are free to move through any of the set of openings; and the second group of pupae are free to advance along the sieve surface from the first edge towards the second edge.

Example 13. In this example, there is provided a system, comprising: a sieving container comprising: a sieve surface inclined from a first edge of the sieve surface to a second edge of the sieve surface; a perimeter wall enclosing the sieve surface to define an interior volume of the sieving container; a funnel positioned adjacent to the second edge of the sieve surface to receive liquid and pupae from an upper surface of the sieve surface, wherein the sieve surface defines a set of openings enabling movement of pupae through the set of openings from the interior volume, individual openings of the set of openings defined by: a length dimension measured along a longitudinal axis of a respective opening; and a width dimension measured along a transverse axis of the respective opening, the width dimension corresponding to a cephalothorax width of a pupa, and the length dimension greater than the width dimension; an actuation system connected to the sieving container, the actuation system configured to separate a population of pupae introduced into the sieving container based on size by moving the sieving container along a substantially vertical lifting axis between a first position and a second position; and a basin comprising an outer wall and a bottom that together define a basin volume with an opening opposite the bottom, the basin sized to receive the sieving container and to retain a liquid.

Example 14. In this example, there is provided a system of any of the preceding or subsequent examples, wherein, when the sieve surface is submerged in the liquid: a first pupae having a first cephalothorax width that is less than the width dimension is free to move through any one of the set of openings; and a second pupae having a second cephalothorax width that is greater than the width dimension is prevented from moving through any one of the set of openings.

Example 15. In this example, there is provided a system of any of the preceding or subsequent examples, wherein moving the sieving container along the substantial vertical lifting axis between the first position and the second position is configured to cyclically submerge the sieve surface in the liquid, wherein an upper portion of the perimeter wall is not submerged in the liquid while the sieve surface is cyclically submerged.

Example 16. In this example, there is provided a system of any of the preceding or subsequent examples, wherein moving the sieving container along the substantially vertical lifting axis between the first position and the second position is configured to advance the population of pupae along the sieve surface towards the funnel.

Example 17. In this example, there is provided a system of any of the preceding or subsequent examples, further comprising an inlet hose that provides a flow of water and pupae to the interior volume of the sieving container.

Example 18. In this example, there is provided a system of any of the preceding or subsequent examples, wherein the population of pupae is carried along the sieve surface from the first edge towards the second edge by a flow of water.

Example 19. In this example, there is provided a system of any of the preceding or subsequent examples, wherein the population of pupae is continuously introduced into the sieving container at a liquid inlet positioned adjacent the first edge of the sieve surface.

Example 20. In this example, there is provided a system of any of the preceding or subsequent examples, wherein the basin comprises a level sensor and a controllable outlet, wherein the controllable outlet is actuated based on a signal from the level sensor to maintain a liquid level within the basin.

Example 21. In this example, there is provided a system of any of the preceding or subsequent examples, wherein the basin comprises two internal dividers defining three compartments within the basin, each of the two internal dividers extending partially up a height of the basin, and wherein each of the three compartments comprises a liquid outlet, the liquid outlet coupled to a center compartment of the three compartments comprises a valve with a controllable solenoid configured to selectively actuate to control a liquid level in the center compartment.

Example 22. In this example, there is provided a system of any of the preceding or subsequent examples, wherein a width of the center compartment is greater than a width of the sieving container, and wherein when the sieving container is submerged in the liquid, the liquid level in the center compartment temporarily raises as the liquid is displaced by the sieving container to cause at least a portion of the liquid to spill over at least one of the two internal dividers and carry pupae from the center compartment to a side compartment of the basin.

Example 23. In this example, there is provided a system of any of the preceding or subsequent examples, wherein the side compartment defines a second liquid outlet different from the liquid outlet, the second liquid outlet configured to enable pupae that pass through the openings to exit the basin.

Example 24. In this example, there is provided a system of any of the preceding or subsequent examples, wherein the two internal dividers extend a first dimension from the bottom of the basin, and wherein the valve is selectively controlled to maintain the liquid level in the basin such that the liquid level is greater than the first dimension when the sieving container is submerged in the liquid.

Example 25. In this example, there is provided a device of any of the preceding or subsequent examples, wherein the actuation system comprises: a vertical rail extending in a vertical direction that corresponds to the substantially vertical lifting axis; a first carrier slidably attached to the vertical rail and attached to the sieving container; and a first actuator device configured to move the first carrier along the vertical rail to cause the sieving container to move along the substantially vertical lifting axis.

Example 26. In this example, there is provided a device of any of the preceding or subsequent examples, further comprising a computing device in electrical communication with the system, the computing device configured to manage operation of the system.

Example 27. In this example, there is provided a method comprising: providing an inclined sieving container within a basin, the inclined sieving container comprising a sieving surface, a perimeter wall enclosing the sieving surface to define an interior volume of the inclined sieving container, and an outlet, the sieve surface inclined with respect to a horizontal axis from a first edge of the sieve surface to a second edge of the sieve surface, wherein the outlet is positioned adjacent the second edge and the sieve surface defines a plurality of elongated openings enabling movement of insect pupae through the plurality of elongated openings from the interior volume, a width dimension of at least one of the elongated openings corresponding to a cephalothorax width of a representative insect pupa; adding a liquid to the basin such that at least a portion of the sieve surface is submerged in the liquid; introducing an aqueous solution comprising a population of pupae into the inclined sieving container at or near the first edge of the sieve surface; performing a sieving action to as to separate the population of pupae into a first group of pupae and a second group of pupae; and maintaining a level of the liquid within the basin as the aqueous solution is added into the inclined sieving container.

Example 28. In this example, there is provided a method of any of the preceding or subsequent examples, wherein maintaining the level of the liquid comprises providing a control signal to an outlet valve of the basin to maintain the level of the liquid within the basin.

Example 29. In this example, there is provided a method of any of the preceding or subsequent examples, wherein performing the sieving action causes the first group of pupae moving into the liquid that is outside the interior volume of the inclined sieving container and the second group of pupae remaining within the interior volume of the inclined sieving container and advancing along the sieve surface to the outlet.

Example 30. In this example, there is provided a method of any of the preceding or subsequent examples, wherein performing the sieving action comprises: priming the outlet by moving the inclined sieving container between a first position and a second position, the inclined sieving container entirely out of the liquid when at the first position and at least partially submerged when at the second position; and cyclically moving the inclined sieving container between the second position and a third position after priming the outlet, the second edge of the sieve surface submerged when at the third position with the third position vertically above the second position.

Example 31. In this example, there is provided a method of any of the preceding or subsequent examples, further comprising: transferring the first group of pupae or the second group of pupae to a different inclined sieving container, the different inclined sieving container comprising a different sieving surface in which is formed a different plurality of elongated openings that includes openings that are sized differently from the openings of the plurality of elongated openings of the sieving surface; and performing a different sieving action using the different inclined sieving container so as to separate the first group of pupae or the second group of pupae into a first subgroup of pupae and a second subgroup of pupae.

Example 32. In this example, there is provided a method of any of the preceding or subsequent examples, wherein performing the sieving action comprises actuating an actuation system connected to the inclined sieving container to move the inclined sieving container vertically between a first position and a second position.

Example 33. In this example, there is provided a device of any of the preceding or subsequent examples, wherein moving the inclined sieving container vertically between the first position and the second position comprises submerging the sieving surface of the inclined sieving container into the liquid.

Example 34. In this example, there is provided a device of any of the preceding or subsequent examples, wherein submerging the sieving surface into the liquid causes an individual pupa of the population of pupae to pass through an elongated opening of the plurality of elongated openings when the pupa is oriented with a narrowest dimension of its cephalothorax aligned with the width dimension of the plurality of elongated openings.

Example 35. In this example, there is provided a device of any of the preceding or subsequent examples, wherein submerging the sieving surface into the liquid causes individual insect pupae to orient in any one of a tail-up orientation or a tail-down orientation.

Example 36. In this example, there is provided a non-transitory computer-readable storage device comprising computer-executable instructions that, when executed by a computer system, cause the computer system to perform operations comprising: actuate an inlet valve providing a liquid and a population of pupae into an inclined sieving container within a basin, the inclined sieving container comprising a sieving surface and a perimeter wall enclosing the sieving surface to define an interior volume of the inclined sieving container, and an outlet, the sieve surface inclined with respect to a horizontal axis from a first edge of the sieve surface to a second edge of the sieve surface, wherein the outlet is positioned adjacent the second edge and the sieve surface defines a plurality of elongated openings enabling movement of insect pupae through the plurality of elongated openings from the interior volume, a width dimension of the at least one of the plurality of elongated openings corresponding to a width of a representative pupa; actuate an outlet valve of the basin such that at least a portion of the sieve surface is submerged in the liquid; and provide a signal to an actuation system to cause the actuation system to perform a sieving action with the inclined sieving container so as to separate the population of pupae into a first group of pupae and a second group of pupae.

Example 37. In this example, there is provided a non-transitory computer-readable storage device of any of the preceding or subsequent examples, wherein providing the signal to the actuation system comprises causing the actuation system to: prime the outlet by moving the inclined sieving container between a first position and a second position, the inclined sieving container entirely out of the liquid when at the first position and at least partially submerged when at the second position; and cyclically move the inclined sieving container between the second position and a third position after priming the outlet, the second edge of the sieve surface submerged when at the third position with the third position vertically above the second position.

Example 38. In this example, there is provided a non-transitory computer-readable storage device of any of the preceding or subsequent examples, wherein the computer-executable instructions further cause a computer system to: convey a signal to actuate a second inclined sieving container, the second inclined sieving container comprising a second sieving surface in which is formed a second plurality of elongated openings that includes openings that are sized differently from the openings of the plurality of elongated openings of the sieving surface, the second inclined sieving container receiving an input of liquid with inset pupae from the outlet of the inclined sieving container; and wherein actuating the second inclined sieving container comprises performing a second sieving action using the second inclined sieving container so as to separate the first group of pupae or the second group of pupae into a first subgroup of pupae and a second subgroup of pupae.

Example 39. In this example, there is provided a non-transitory computer-readable storage device of any of the preceding or subsequent examples, wherein the signal to the actuation system causes the actuation system to move the inclined sieving container vertically between a first position and a second position.

Example 40. In this example, there is provided a non-transitory computer-readable storage device of any of the preceding or subsequent examples, wherein moving the inclined sieving container vertically between the first position and the second position comprises submerging the sieving surface of the inclined sieving container into the liquid.

Example 41. In this example, there is provided a non-transitory computer-readable storage device of any of the preceding or subsequent examples, wherein submerging the sieving surface into the liquid causes individual pupae of the population of pupae to pass through the plurality of elongated openings when the individual pupae are oriented with a narrowest dimension of their cephalothoraxes aligned with the width dimension of the plurality of elongated openings.

Example 42. In this example, there is provided a system comprising: a mobile cabinet; an actuation system connected to an upper portion of the mobile cabinet; a sieving container connected to the actuation system and housed within the mobile cabinet, the sieving container comprising: a sieve surface and a perimeter wall enclosing the sieve surface to form an interior volume of the sieving container, the sieve surface inclined from a first edge of the sieve surface to a second edge of the sieve surface, the sieve surface defining a set of openings enabling movement of pupae through the set of openings from the interior volume of the sieving container, individual openings of the set of openings defined by: a length dimension measured along a longitudinal axis of a respective opening; and a width dimension measured along a transverse axis of the respective opening; an outlet coupled to the second edge of the sieve surface to receive liquid and pupae from an upper surface of the sieve surface; and a basin attached to the mobile cabinet and comprising an outer wall and a bottom that together define a basin volume with an opening opposite the bottom, the basin sized to receive the sieving container and to retain a liquid, wherein the actuation system is configured to separate a population of pupae introduced into the interior volume of the sieving container based on size by moving the sieving container along a substantially vertical lifting axis between a first position within the basin and a second position within the basin.

Example 43. In this example, there is provided a system of any of the preceding or subsequent examples, wherein the sieve surface is inclined such that a first height of the first edge is greater than a second height of the second edge of the sieve surface.

Example 44. In this example, there is provided a system of any of the preceding or subsequent examples, wherein a pupae is advanced along the sieve surface by moving the sieving container along the substantially vertical lifting axis between the first position and the second position to submerge the pupae and the sieve surface into the liquid.

While the present subject matter has been described in detail with respect to specific embodiments thereof, it will be appreciated that those skilled in the art, upon attaining an understanding of the foregoing may readily produce alterations to, variations of, and equivalents to such embodiments. Accordingly, it should be understood that the present disclosure has been presented for purposes of example rather than limitation, and does not preclude inclusion of such modifications, variations, and/or additions to the present subject matter as would be readily apparent to one of ordinary skill in the art. Indeed, the methods and systems described herein may be embodied in a variety of other forms; furthermore, various omissions, substitutions and changes in the form of the methods and systems described herein may be made without departing from the spirit of the present disclosure. The accompanying claims and their equivalents are intended to cover such forms or modifications as would fall within the scope and spirit of the present disclosure.

The foregoing description of some examples has been presented only for the purpose of illustration and description and is not intended to be exhaustive or to limit the disclosure to the precise forms disclosed. Numerous modifications and adaptations thereof will be apparent to those skilled in the art without departing from the spirit and scope of the disclosure.

Reference herein to an example or implementation means that a particular feature, structure, operation, or other characteristic described in connection with the example may be included in at least one implementation of the disclosure. The disclosure is not restricted to the particular examples or implementations described as such. The appearance of the phrases "in one example," "in an example," "in one implementation," or "in an implementation," or variations of the same in various places in the specification does not necessarily refer to the same example or implementation. Any particular feature, structure, operation, or other characteristic described in this specification in relation to one example or implementation may be combined with other features, structures, operations, or other characteristics described in respect of any other example or implementation.

Use herein of the word "or" is intended to cover inclusive and exclusive OR conditions. In other words, A or B or C includes any or all of the following alternative combinations as appropriate for a particular usage: A alone; B alone; C alone; A and B only; A and C only; B and C only; and all three of A and B and C.

What is claimed is:

1. A method, comprising:
providing an inclined sieving container within a basin, the inclined sieving container comprising a sieving surface, a perimeter wall enclosing the sieving surface to define an interior volume of the inclined sieving container, and an outlet, the sieve surface inclined with respect to a horizontal axis from a first edge of the sieve surface to a second edge of the sieve surface, wherein the outlet is positioned adjacent the second edge and the sieve surface defines a plurality of elongated openings enabling movement of insect pupae through the plurality of elongated openings from the interior volume, a width dimension of at least one of the elongated openings corresponding to a cephalothorax width of a representative insect pupa;
adding a liquid to the basin such that at least a portion of the sieve surface is submerged in the liquid;
introducing an aqueous solution comprising a population of pupae into the inclined sieving container at or near the first edge of the sieve surface;
performing a sieving action to separate the population of pupae into a first group of pupae and a second group of pupae; and
maintaining a level of the liquid within the basin as the aqueous solution is added into the inclined sieving container.

2. The method of claim 1, wherein maintaining the level of the liquid comprises providing a control signal to a liquid outlet valve of the basin to maintain the level of the liquid within the basin.

3. The method of claim 1, wherein performing the sieving action causes the first group of pupae to move into the liquid that is outside the interior volume of the inclined sieving container and the second group of pupae to remain within the interior volume of the inclined sieving container and to advance along the sieve surface towards the outlet.

4. The method of claim 1, wherein performing the sieving action comprises:
priming the outlet by moving the inclined sieving container between a first position and a second position, the inclined sieving container entirely out of the liquid when at the first position and at least partially submerged when at the second position; and
cyclically moving the inclined sieving container along a substantially vertical lifting axis between the second position and a third position after priming the outlet, the second edge of the sieve surface submerged when at the third position with the third position vertically above the second position.

5. The method of claim 1, further comprising:
transferring the first group of pupae or the second group of pupae to a different inclined sieving container, the different inclined sieving container comprising a different sieving surface in which is formed a different plurality of elongated openings that includes openings that are sized differently from the openings of the plurality of elongated openings of the sieving surface; and
performing the sieving action using the different inclined sieving container so as to separate the first group of pupae or the second group of pupae into a first subgroup of pupae and a second subgroup of pupae.

6. The method of claim 5, wherein submerging the sieving surface into the liquid causes at least one individual pupa of the population of pupae to pass through an elongated opening of the plurality of elongated openings when the pupa is oriented with a narrowest dimension of its cephalothorax aligned with the width dimension of the plurality of elongated openings.

7. The method of claim 1, wherein performing the sieving action comprises moving the inclined sieving container with respect to the basin in at least one of a vertical or a horizontal direction.

8. A non-transitory computer-readable storage device comprising computer-executable instructions that, when executed by a computer system, cause the computer system to:
actuate an inlet valve providing a liquid and a population of pupae into an inclined sieving container within a basin, the inclined sieving container comprising:
a sieving surface and a perimeter wall enclosing the sieving surface to define an interior volume of the inclined sieving container, and an outlet, the sieve surface inclined with respect to a horizontal axis from a first edge of the sieve surface to a second edge of the sieve surface,
wherein the outlet is positioned adjacent to the second edge and the sieve surface defines a plurality of elongated openings enabling movement of insect pupae through the plurality of elongated openings from the interior volume, a width dimension of the at least one of the plurality of elongated openings corresponding to a width of a representative pupa;
actuate an outlet valve of the basin such that at least a portion of the sieve surface is submerged in the liquid; and
provide one or more signals to an actuation system to cause the actuation system to perform a sieving action with the inclined sieving container to separate the population of pupae into a first group of pupae and a second group of pupae.

9. The non-transitory computer-readable storage device of claim 8, wherein the one or more signals further cause the actuation system to:
prime the outlet by moving the inclined sieving container between a first position and a second position, the inclined sieving container entirely out of the liquid when at the first position and at least partially submerged when at the second position; and
cyclically move the inclined sieving container between the second position and a third position after priming the outlet, the second edge of the sieve surface submerged when at the third position with the third position vertically above the second position.

10. The non-transitory computer-readable storage device of claim 8, wherein the one or more signals to the actuation system to cause the actuation system to move the inclined sieving container vertically between a first position and a second position.

11. The non-transitory computer-readable storage device of claim 10, wherein moving the inclined sieving container vertically between the first position and the second position comprises submerging the sieving surface of the inclined sieving container into the liquid.

12. The non-transitory computer-readable storage device of claim 11, wherein submerging the sieving surface into the liquid causes individual pupae of the population of pupae to pass through the plurality of elongated openings when the individual pupae are oriented with a narrowest dimension of their cephalothoraxes aligned with the width dimension of the plurality of elongated openings.

13. The non-transitory computer-readable storage device of claim 8, wherein causing the actuation system to perform the sieving action comprises moving the inclined sieving container with respect to the basin in at least one of a vertical or a horizontal direction.

14. A method, comprising:
provviding a sieving surface within a basin, the sieving surface defining a porous boundary between a first and a second volume within the basin, the sieving surface inclined with respect to a horizontal axis from a first edge of the sieving surface to a second edge of the sieving surface, wherein the sieving surface defines a plurality of elongated openings enabling movement of insect pupae through the plurality of elongated openings, a width dimension of at least one of the elongated openings corresponding to a cephalothorax width of a representative insect pupa;
directing a flow of an aqueous solution comprising a population of pupae into the basin and against the sieving surface;
performing a sieving action by moving the sieving surface with respect to the basin to separate the population of pupae into a first group of pupae and a second group of pupae; and
maintaining a level of a liquid within the basin as the aqueous solution is added.

15. The method of claim 14, wherein performing the sieving action comprises moving the sieving surface in a first direction parallel with a vertical axis of the basin.

16. The method of claim 15, wherein performing the sieving action comprises moving the sieving surface in a second direction parallel the horizontal axis.

17. The method of claim 14, wherein performing the sieving action causes the first group of pupae to move through the porous boundary from the first volume to the second volume.

18. The method of claim 14, wherein performing the sieving action comprises:
priming an outlet of the basin by moving the sieving surface between a first position and a second position, the sieving surface entirely out of the liquid when at the first position and at least partially submerged when at the second position; and
cyclically moving the sieving surface along a substantially vertical lifting axis between the second position and a third position after priming the outlet, the second edge of the sieving surface submerged when at the third position with the third position vertically above the second position.

19. The method of claim 14, wherein performing the sieving action comprises causing an actuation system to move the sieving surface vertically between a first position and a second position.

20. A non-transitory computer-readable storage device comprising computer-executable instructions that, when executed by a computer system, cause the computer system to:
direct a flow of an aqueous solution comprising a population of pupae into a basin and against a sieving surface within the basin, the sieving surface defining a porous boundary between a first and a second volume within the basin, the sieving surface inclined with respect to a horizontal axis from a first edge of the sieving surface to a second edge of the sieving surface, wherein the sieving surface defines a plurality of elongated openings enabling movement of insect pupae through the plurality of elongated openings, a width dimension of at least one of the plurality of elongated openings corresponding to a cephalothorax width of a representative insect pupa;
perform a sieving action by moving the sieving surface with respect to the basin to separate the population of pupae into a first group of pupae and a second group of pupae; and
maintain a level of liquid within the basin as the aqueous solution is added.

* * * * *